(12) United States Patent
Brinker et al.

(10) Patent No.: US 9,855,217 B2
(45) Date of Patent: Jan. 2, 2018

(54) TOROIDAL MESOPOROUS SILICA NANOPARTICLES (TMSNPS) AND RELATED PROTOCELLS

(71) Applicants: STC.UNM, Albuquerque, NM (US); National Technology & Engineering Solutions of Sandia, LLC, Albuquerque, NM (US)

(72) Inventors: C. Jeffrey Brinker, Albuquerque, NM (US); Yu-Shen Lin, Albuquerque, NM (US)

(73) Assignees: STC. UNM, Albuquerque, NM (US); National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/023,110

(22) PCT Filed: Sep. 18, 2014

(86) PCT No.: PCT/US2014/056342
§ 371 (c)(1),
(2) Date: Mar. 18, 2016

(87) PCT Pub. No.: WO2015/042279
PCT Pub. Date: Mar. 26, 2015

(65) Prior Publication Data
US 2016/0338954 A1    Nov. 24, 2016

Related U.S. Application Data

(60) Provisional application No. 61/879,540, filed on Sep. 18, 2013.

(51) Int. Cl.
| | |
|---|---|
| A61K 9/14 | (2006.01) |
| A61K 9/127 | (2006.01) |
| A61K 31/7088 | (2006.01) |
| B82Y 5/00 | (2011.01) |
| A61K 9/51 | (2006.01) |
| A61K 38/16 | (2006.01) |
| A61K 38/43 | (2006.01) |
| A61K 39/395 | (2006.01) |
| C12N 15/88 | (2006.01) |
| B82Y 15/00 | (2011.01) |

(52) U.S. Cl.
CPC .............. *A61K 9/1271* (2013.01); *A61K 9/14* (2013.01); *A61K 9/5115* (2013.01); *A61K 9/5123* (2013.01); *A61K 31/7088* (2013.01); *A61K 38/16* (2013.01); *A61K 38/43* (2013.01); *A61K 39/395* (2013.01); *B82Y 5/00* (2013.01); *C12N 15/88* (2013.01); *B82Y 15/00* (2013.01)

(58) Field of Classification Search
None
See application file for complete search history.

(56) References Cited

U.S. PATENT DOCUMENTS

2002/0147105 A1    10/2002    Shamshoum et al.

FOREIGN PATENT DOCUMENTS

WO    2013056132 A2    4/2013

OTHER PUBLICATIONS

Fang et al., Chem. Mater., 2011, 23, 4660-4662.*
Zapryanova et al., Journal of Materials Science, 1979, 14, 1175-1178.*
Iskandar et al., Journal of Colloid and Interface Science, 2003, 265, 296-303.*
Dengler EC, et al. Mesoporous silica-supported lipid bilayers (protocells for DNA cargo delivery to the spinal cord. Journal of Controlled Release, 2013;168:209-224. See abstract, pp. 210, 211, 213 and 214: and Figure 1.
Li Z, et al. Mesoporous silica nanoparticles in biomedical applications. Chemical Society Reviews, 2012;41:2590-2605. See abstract: and pp. 2594, 2600 and 2604.
Suteewong T, et al. Synthesis and formation mechanism of aminated mesoporous silica nanoparticles. Chemistry of Materials, 2012;24:3895-3905. See abstract.
"European Application Serial No. 14845415.0, Response filed Nov. 2, 2016 to Communication pursuant to Rules 161(1) and 162 EPC dated May 2, 2016", 9 pgs.
Attard, George S, et al., "Liquid-crystalline phases as templates for the synthesis of mesoporous silica", Nature Publishing Group vol. 378, (Nov. 23, 1995), 3 pgs.
Feng, Pingyun, et al., "Control of Pore Sizes in Mesoporous Silica Templated by Liquid Crystals in Block Copolymer-Cosurfactant-Water Systems", Langmuir, vol. 16, No. 12,, (Mar. 24, 2000), 7 pgs.
Huo, Qisheng, et al., "Surfactant Control of Phases in the Synthesis of Mesoporous Silica-Based Materials", Chem. Mater. 1996, 8, (Feb. 15, 1996), 14 pgs.
Schiller, Renate, et al., "Synthesis of Mesoporous Silica Particles and Capsules by Miniemulsion Technique", Chem. Mater. 2009, 21,, (Sep. 23, 2009), 11 pgs.

* cited by examiner

*Primary Examiner* — Abigail Vanhorn
(74) *Attorney, Agent, or Firm* — Schwegman Lundberg & Woessner, P.A.

(57) ABSTRACT

In one aspect, the invention provides novel monodisperse, colloidally-stable, toroidal mesoporous silica nanoparticles (TMSNPs) which are synthesized from ellipsoid-shaped mesoporous silica nanoparticles (MSNPs) which are prepared using an ammonia basecatalyzed method under a low surfactant conditions. Significantly, the TMSNPs can be loaded simultaneously with a small molecule active agent, a siRNA, a mRNA, a plasmid and other cargo and can be used in the diagnosis and/or treatment of a variety of disorders, including a cancer, a bacterial infection and/or a viral infection, among others. Related protocells, pharmaceutical compositions and therapeutic and diagnostic methods are also provided.

18 Claims, 24 Drawing Sheets

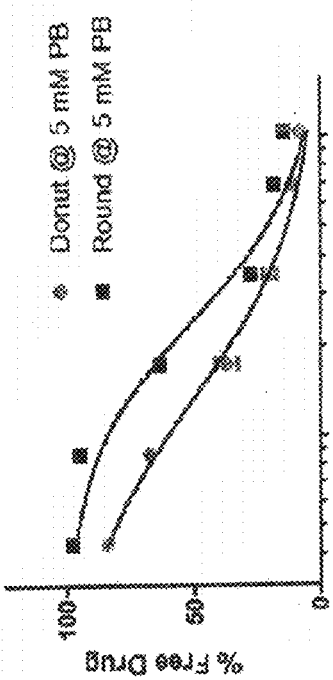
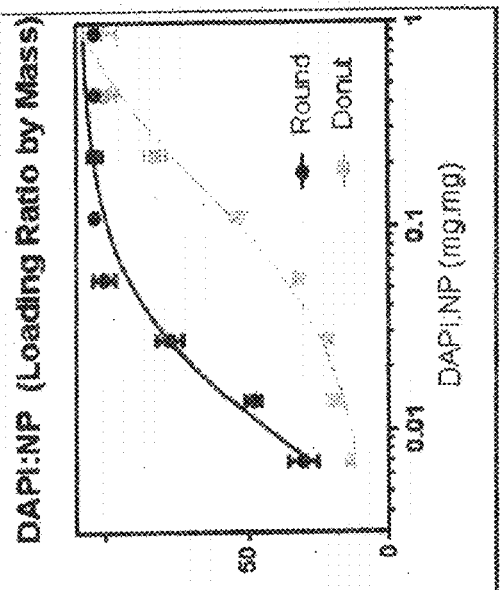
Figure 6

Beyond Small Molecules – DNA Plasmid Delivery in Vivo

- Large pore (20-30 nm) MSNPs
  - Commonly used to load nucleic acid cargos, however, we have found synthesis methods are unreliable and particles often aggregate.

- Torus shaped MSNPs are of interest due to high stability, 3 different pore sizes and ability to be coated by a lipid bilayer. Also, potentially unique loading method of wrapping around torus.

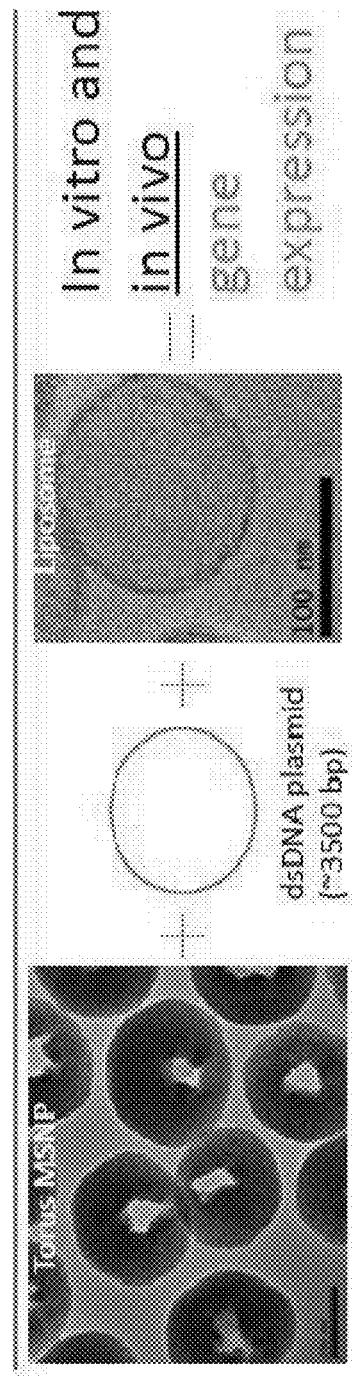

Fig. 14

FIGURE 18
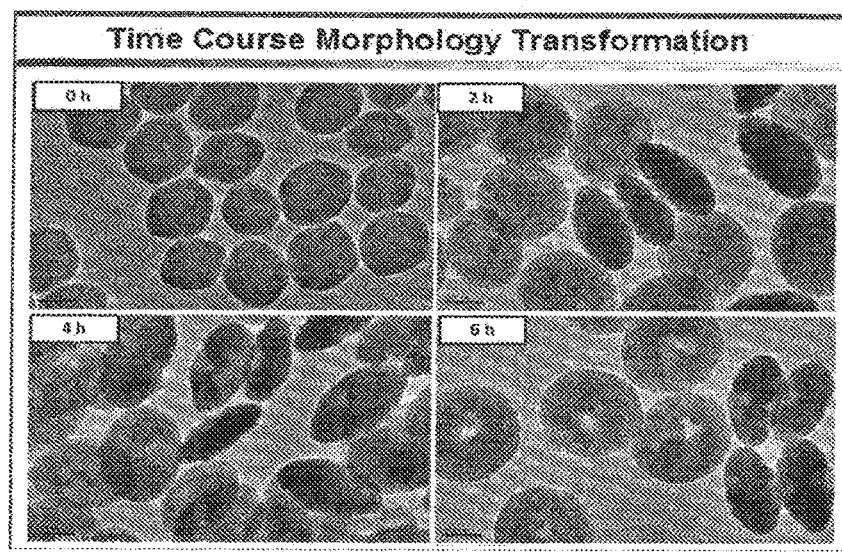
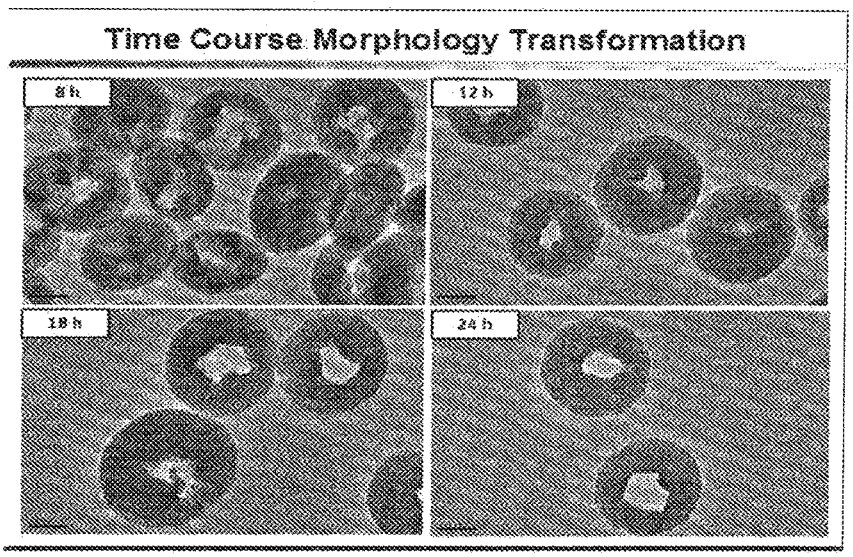

TOROIDAL MESOPOROUS SILICA NANOPARTICLES (TMSNPS) AND RELATED PROTOCELLS

CROSS-REFERENCE TO RELATED APPLICATIONS

This application is a U.S. national phase patent application based upon international patent application no. PCT/US14/56342 filed Sep. 18, 2014, which claims priority from U.S. Provisional Patent Application Serial No. 61/879,540, filed Sep. 18, 2013, and entitled Synthesis of Torus ("Donut") Shaped MSNP and Resultant Pore Size Distribution", both of which applications are hereby incorporated by reference in their entirety herein.

STATEMENT REGARDING FEDERAL FUNDING

This invention was made with government support under DE-AC04-94AL85000 awarded by the U.S. Department of Energy and U01 CA15179201 awarded by the National Institutes of Health. The government has certain rights in the invention.

FIELD OF THE INVENTION

In one aspect, the invention provides novel monodisperse, colloidally-stable, toroidal mesoporous silica nanoparticles (TMSNPs) which are synthesized from ellipsoid-shaped mesoporous silica nanoparticles (MSNPs) which are prepared using an ammonia base-catalyzed method under a low surfactant conditions. Significantly, the TMSNPs can be loaded simultaneously with a small molecule active agent, a siRNA, a mRNA and a plasmid and can be used in the diagnosis and/or treatment of a variety of disorders, including a cancer, a bacterial infection and/or a viral infection.

Related protocells, pharmaceutical compositions and therapeutic and diagnostic methods are also provided.

BACKGROUND OF THE INVENTION

Nanoparticle (NP)/cell interactions, particularly in complex in vivo microenvironments, are regulated by an intricate spatiotemporal interplay of numerous biological and NP characteristics. Multiple NP physicochemical properties including, at the most basic level, material composition, size, shape, surface charge, and surface chemistry, have all been reported to play significant roles.[1-3] However, the relative importance of these diverse NP physicochemical properties in regulating interactions with various biological systems remains incompletely understood.[1] As such, achieving or avoiding cell-type specific interactions in vivo requires an improved understanding of the relative roles of these diverse NP properties, as well an ability to exert a high level of control over these properties during NP synthesis.

While the existing paradigm dictates that decreased size, neutral or negative zeta ($\zeta$) potential, and extent of PEGylation are correlated with increased circulation time (i.e., reduced interaction with host cells),[4] the manner in which these combined physicochemical properties conspire to direct in vivo cellular interactions has not been elucidated through careful systematic studies, and the nature of these interactions is likely to vary significantly by particle formulation and cell type.

An ability to simultaneously load NP's with a variety of diagnostic and/or therapeutic agents and to more effectively exploit NP shape and pore size would facilitate the identification and treatment of a numerous disorders, including cancers and bacterial and viral infections.

SUMMARY OF THE INVENTION

In one embodiment, the invention provides a population of monodisperse, colloidally-stable, torroidal mesoporous silica nanoparticles (TMSNPs) which are optionally modified with SiOH/PEG and which are further optionally aminated, wherein the MSNPs have: (a) a diameter ranging from about 25 nm to about 300 nm, or from about 25 nm to about 200 nm, or from about 25 nm to about 100 nm, or from about 25 nm to about 95, 90, 85, 80, 75, 70, 65, 60, 55, 50, 45, 40, 35 or 30 nm (more preferably, less than 50 nm, even more preferably, less than 30, 25, 20, 15 or 10 nm) (b) a plurality of at least three distinct pore sizes, each of which vary between about 1 nm to about 200 nm or from about 1 nm to about 100 nm, or from about 1 nm to about 95, 90, 85, 80, 75, 70, 65, 60, 55, 50, 45, 40, 35 or 30 nm (or less than 50, 40, 30, 25, 20, 15, 10, 9, 8, 7, 6, 5, 4, 3, 2 or 1 nm) (c) a surface area of between about 100-1,000 m$^2$/g and a Zeta potential ($\zeta$) of between about −40 mV to about +40 mV (more preferably less than 0 mV) and wherein the TMSNPs are synthesized from ellipsoid-shaped mesoporous silica nanoparticles (MSNPs) which are prepared preferably using an ammonia base-catalyzed method under a low surfactant conditions.

Preferably, the ammonia base-catalyzed method includes the step of reacting tetraethyl orthosilicate (TEOS) with a mixture of n-cetyltrimethylammonium bromide (CTAB) and NH$_4$OH and heating the resultant product in a hydrothermaton step for a period of between about 10 to about 30 hours at a temperature of between about 30° C. to about 50° C. to yield an ellipsoid shaped mesoporous silica particle solution. This reaction can be done one-pot or in steps. The ellipsoid shaped mesoporous silica particle solution is then hydrothermally treated by heating at a temperature of between about 100° C. to about 150° C. (more preferably about 120° C.) to yield the TMSNPs. Preferably, the TMSNPs are aminated with an aminating agent which does not comprise a primary amine group, e.g. N trimethoxysilylpropyl-N,N,N-trimethyl ammonium chloride (TMAC-silane, MW 258).

Notably, TMSNPs of the invention can be loaded simultaneously with a small molecule active agent, a siRNA, a mRNA and a plasmid. For example, the TMSNPs' may be loaded with at least one macromolecule selected from the group consisting of a nucleic acid, small molecule active agent, polypeptide/protein or a carbohydrate. Examples of such cargo include RNA, such as mRNA, siRNA, shRNA micro RNA, a protein, including a protein toxin (e.g. ricin toxin A-chain or diphtheria toxin A-chain) and/or DNA (including double stranded or linear DNA, minicircle DNA, plasmid DNA which may be supercoiled and/or packaged (e.g. with histones) and which may be optionally modified with a nuclear localization sequence). In some embodiments, simultaneous loading of a small molecule active agent, a siRNA, shRNA, mRNA, microRNA, minicircle DNA and a plasmid is achieved by loading each of the distinct cargo components in differently sized pores of "triphasic (+)" TMSNPs. In other embodiments, one or more cargo components is loaded either exclusively onto the TMSNP surface or is loaded through pore and/or surface loading.

In certain embodiments, the surface of the TMSNPs is complexed with: (a) a nucleic acid that encodes a siRNA (preferably a siRNA that suppresses gene expression in human tumor cells) operatively linked with a promoter; and (b) a cancer cell targeting ligand. The nucleic acid can be dsDNA and the cancer cell targeting ligand can be a tumor-targeting human monoclonal antibody or a single-chain variable fragment (scFv) thereof. The TMSNPs can also be complexed with one or more additional anti-cancer agents.

In other embodiments, the TMSNPs are loaded with: a cell targeting species (e.g. a targeting peptide such as a SP94 peptide or a MET binding peptide) and at least one cargo component selected from the group consisting of a polynucleotide, e.g., double stranded linear DNA, minicircle DNA, plasmid DNA (which (1) can be optionally modified to express a nuclear localization sequence (2) can be supercoiled and/or packaged plasmid DNA (3) can be histone-packaged supercoiled plasmid DNA comprising a mixture of human histone proteins (4) may be capable of expressing a polypeptide toxin (e.g. ricin toxin chain-A or diphtheria toxin chain-A)), a messenger RNA, a small hairpin RNA (shRNA), a small interfering RNA (siRNA)) or microRNA, a drug, an imaging agent (e.g. green fluorescent protein or red fluorescent protein) or a mixture thereof, and wherein one of said cargo components is optionally conjugated further with a nuclear localization sequence. In some embodiments, the shRNA and siRNA induce cell apoptosis.

The invention also includes protocells in which the novel TMSNPs described herein are encapsulated within a lipid bi- or multilayer, and pharmaceutical compositions comprising the TMSNPs and protocells. Methods of treating a variety of disorders, including a cancer and bacterial and viral infections are also provided.

In addition to providing a greater pore size distribution (at least three distinct pore sizes) and improved stability (over one year in solution), our TMSNPs and protocells, when compared to traditionally configured NP's, exhibit a significantly greater cargo capacity that facilitates delivery of compositions such as dsDNA plasmids to a variety of cells in vitro and in vivo. Interior pore size of the TMSNPs can be controlled; syntheses as described herein can also yield bi-concave shaped MSNPs as intermediate products and can generate TMSNPs having multiple concave pores. Despite the irregular shape of the TMSNPs, they can be uniformly coated in a lipid bi- or multilayer to yield protocells as described herein.

While not wishing to be bound by any theory, the improved cellular uptake evidenced by TMSNPs and protocells of the invention may be due in part to a minimization of perpendicular fluid mechanical forces attributable to the TMSNPs' and protocells' increased surface area.

Our ability to vary size, charge, charge exposure and PEGylation of the TMSNPs and protocells described herein can be controlled to such an extent that specifically tuned particles can be controllably deposited within certain tissue types (e.g. to a tumor). By modifying TMSNP core (size, shape, mass) and surface properties, we can alter in vivo biodistribution by changing the proportion of particles arrested in different types of cells and tissues. This control over the particles allows for precise physiochemical targeting of specific cell and tissue types.

In certain preferred embodiments, the MSNPs, in particular, torus protocells according to the present invention, are potentially quite useful for the delivery of larger nucleic acids (from 100 nucleotide bases to more than 1000 kb, about 1 kb-1000 kb, about 2 kb to about 750 kb, about 5 kb to about 500 kb, about 10 kb to about 250 kb, about 25 kb to about 200 kb) (e.g. double stranded DNA, plasmid DNA, mini-circle DNA, naked DNA, and messenger RNA), as well as for larger polypeptides or proteins (from 25 amino acids to more than 5000 aa, about 50 aa-1000 aa, about 75 aa to about 750 aa, about 100 aa 500 a, about 35 aa to about 250 aa, about 30 aa to about 200 aa).

In a process embodiment, a method of preparing the torroidal nanoparticles pursuant to the present invention involves providing a solution of ellipsoid-shaped mesoporous silica nanoparticles (MSNPs) (which are prepared preferably using an ammonia base-catalyzed method under low surfactant conditions and heat) and hydrothermally treating the ellipsoid shaped mesoporous silica particle solution by heating the solution at a temperature of between about 100° C. to about 150° C. to yield the TMSNPs. In this embodiment, a solution of elliptical nanoparticles is prepared from an ammonia base-catalyzed method including the step of reacting tetraethyl orthosilicate (TEOS) with a mixture of n-cetyltrimethylammonium bromide (CTAB) and NH$_4$OH and heating the resultant product for a period of between about 10 to about 30 hours at a temperature of between about 30° C. to about 50° C. to yield said solution, wherein the reaction can be performed in one-pot or in steps. In a further step, the solution is hydrothermally heated between about 100° C. to about 150° C., about 110° to 140°, about 115 to about 135 for a time sufficient to yield the TMSNPs.

In an alternative embodiment, the present invention relates to a process for making a population of monodisperse, colloidally-stable, torroidal mesoporous silica nanoparticles (TMSNPs) which are optionally PEGylated and/or modified with SiOH/PEG and which are optionally aminated, wherein the MSNPs have: (a) a diameter ranging from about 25 nm to about 300 nm, or from about 25 nm to about 200 nm, or from about 25 nm to about 100 nm, or from about 25 nm to about 95, 90, 85, 80, 75, 70, 65, 60, 55, 50, 45, 40, 35 or 30 nm (more preferably, less than 50 nm, even more preferably, less than 30, 25, 20, 15 or 10 nm) (b) a plurality of at least three distinct pore sizes, each of which vary between about 1 nm to about 200 nm, or which vary between about 50, 40, 30, 25, 20, 15, 10, 9, 8, 7, 6, 5, 4, 3, 2 or 1 nm (c) a surface area of between about 100-1,000 m$^2$/g and a Zeta potential (ζ) of between about −40 mV to about +40 mV (more preferably less than 0 mV), the process comprising:

(a) (1) reacting at least one (preferably one) silica precursor selected from the group consisting of tetramethyl orthosilicate (TMOS), tetraethyl orthosilicate (TEOS) and tetrapropyl orthosilicate (TPOS) with a mixture comprised of (i) at least one (preferably one) surfactant selected from the group consisting of polyvinyl alcohol (PVA), dioctyl sodium sulfosuccinate, methyl cellulose, polysorbates, cetyltrimethylammonium bromide (CTAB), dodecylamine (DDA), 1,2-di-O-octadecenyl-3-trimethylammonium propane (DOTMA), and 1,2-Dioleoyl-3-trimethylammonium-propane (DOTAP), and (ii) an ammonia base, and (2) heating the resultant product for a period of between about 10 to about 30 hours, or for about 15 to about 25 hours, or for about 16, 17, 18, 19, 20, 21, 22, 23 or about 24 hours, most preferably for about 20 hours, at a temperature of between about 30° C. to about 50° C., or from about 35° C. to about 45° C., or at about 36° C., 37° C., 38° C., 39° C., 40° C., 41° C., 42° C., 43° C., 44° C. or 45° C., most preferably at about 40° C., to yield an ellipsoid shaped mesoporous silica particle solution; and (b) hydrothermally treating the ellipsoid shaped mesoporous silica particle solution by heating the solution at a temperature of between about 100° C. to about 150° C. (more preferably about between about 110° C. to about 140° C., still more preferably between about 115° C. to about 135° C., still more preferably at about 120° C.) to yield the TMSNPs; wherein the process can be performed in a single (one) pot or in steps. In preferred aspects of this process, (a) the silica precursor is tetraethyl orthosilicate (TEOS); (b) the surfactant is cetyltrimethylammonium bromide (CTAB); and (c) the ammonia base is NH$_4$OH.

In another embodiment, the invention is directed to a population of monodisperse, colloidally-stable, torroidal mesoporous silica nanoparticles (TMSNPs) which are optionally PEGylated and/or modified with SiOH/PEG and which are optionally aminated, wherein the MSNPs have:
(a) a diameter ranging from about 25 nm to about 300 nm, or from about 25 nm to about 200 nm, or from about 25 nm to about 100 nm, or from about 25 nm to about 95, 90, 85, 80, 75, 70, 65, 60, 55, 50, 45, 40, 35 or 30 nm (more preferably, less than 50 nm, even more preferably, less than 30, 25, 20, 15 or 10 nm) (b) a plurality of at least three distinct pore sizes, each of which vary between about 1 nm to about 200 nm, or which vary between about 50, 40, 30, 25, 20, 15, 10, 9, 8, 7, 6, 5, 4, 3, 2 or 1 nm (c) a surface area of between about 100-1,000 m$^2$/g and a Zeta potential ($\zeta$) of between about −40 mV to about +40 mV (more preferably less than 0 mV), wherein the TMSNPs are made by a process comprising:
(a) (1) reacting at least one (preferably one) silica precursor selected from the group consisting of tetramethyl orthosilicate (TMOS), tetraethyl orthosilicate (TEOS) and tetrapropyl orthosilicate (TPOS) with a mixture comprised of (i) at least one (preferably one) surfactant selected from the group consisting of polyvinyl alcohol (PVA), dioctyl sodium sulfosuccinate, methyl cellulose, polysorbates, cetyltrimethylammonium bromide (CTAB), dodecylamine (DDA), 1,2-di-O-octadecenyl-3-trimethylammonium propane (DOTMA), and 1,2-Dioleoyl-3-trimethylammonium-propane (DOTAP), and (ii) an ammonia base, and (2) heating the resultant product for a period of between about 10 to about 30 hours, or for about 15 to about 25 hours, or for about 16, 17, 18, 19, 20, 21, 22, 23 or about 24 hours, most preferably for about 20 hours, at a temperature of between about 30° C. to about 50° C., or from about 35° C. to about 45° C., or at about 36° C., 37° C., 38° C., 39° C., 40° C., 41° C., 42° C., 43° C., 44° C. or 45° C., most preferably at about 40° C., to yield an ellipsoid shaped mesoporous silica particle solution; and
(b) hydrothermally treating the ellipsoid shaped mesoporous silica particle solution by heating the solution at a temperature of between about 100° C. to about 150° C. (more preferably about between about 110° C. to about 140° C., still more preferably between about 115° C. to about 135° C., still more preferably at about 120° C.) to yield the TMSNPs; and wherein the process can be one pot or in steps. In this population of TMSNPs, (a) the silica precursor is tetraethyl orthosilicate (TEOS); (b) the surfactant is cetyltrimethylammonium bromide (CTAB); and (c) the ammonia base is NH$_4$OH.

In still another embodiment, the present invention is directed to a population of monodisperse, colloidally-stable, biconcave mesoporous silica nanoparticles (BMSNPs) which are optionally PEGylated and/or modified with SiOH/PEG and which are optionally aminated, wherein the MSNPs have a diameter ranging from about 25 nm to about 300 nm, or from about 25 nm to about 200 nm, or from about 25 nm to about 100 nm, or from about 25 nm to about 95, 90, 85, 80, 75, 70, 65, 60, 55, 50, 45, 40, 35 or 30 nm (more preferably, less than 50 nm, even more preferably, less than 30, 25, 20, 15 or 10 nm), wherein the BMSNPs are made by a process comprising:
(a) (1) reacting at least one silica precursor selected from the group consisting of tetramethyl orthosilicate (TMOS), tetraethyl orthosilicate (TEOS) and tetrapropyl orthosilicate (TPOS) with mixture comprised of (i) at least one surfactant selected from the group consisting of polyvinyl alcohol (PVA), dioctyl sodium sulfosuccinate, methyl cellulose, polysorbates, cetyltrimethylammonium bromide (CTAB), dodecylamine (DDA), 1,2-di-O-octadecenyl-3-trimethylammonium propane (DOTMA), and 1,2-Dioleoyl-3-trimethylammonium-propane (DOTAP), and (ii) an ammonia base, and (2) heating the resultant product for a period of between about 1, 2, 3, 4, 5, 6, 7 or 8 hours, most preferably for about 5 or about 6 hours, at a temperature of between about 30° C. to about 50° C., or from about 35° C. to about 45° C., or at about 36° C., 37° C., 38° C., 39° C., 40° C., 41° C., 42° C., 43° C., 44° C. or 45° C., most preferably at about 40° C., to yield a biconcave shaped mesoporous silica particle solution; and
(b) hydrothermally treating the biconcave shaped mesoporous silica particle solution by heating the solution at a temperature of between about 100° C. to about 150° C. (more preferably about between about 110° C. to about 140° C., still more preferably between about 115° C. to about 135° C., still more preferably at about 120° C.) to yield the BMSNPs; and wherein the process can be one pot or in steps. In this embodiment, it is preferred that (a) the silica precursor is tetraethyl orthosilicate (TEOS); (b) the surfactant is cetyltrimethylammonium bromide (CTAB); and (c) the ammonia base is NH$_4$OH.

These and other aspects of the invention are described further in the Detailed Description of the Invention.

BRIEF DESCRIPTION OF THE FIGURES

FIG. 6 shows cargo loading of TMSNPs made in accordance with the invention. As determined in the experiment(s) of Example 2.

FIG. 14 depicts in vivo DNA plasmid delivery using TMSNPs and related protocells made in accordance with the invention.

FIG. 18 depicts a time course morphology transformation of TMSNPs made in accordance with the invention. As determined in the experiment(s) of Example 2.

DETAILED DESCRIPTION OF THE INVENTION

Figure 1:
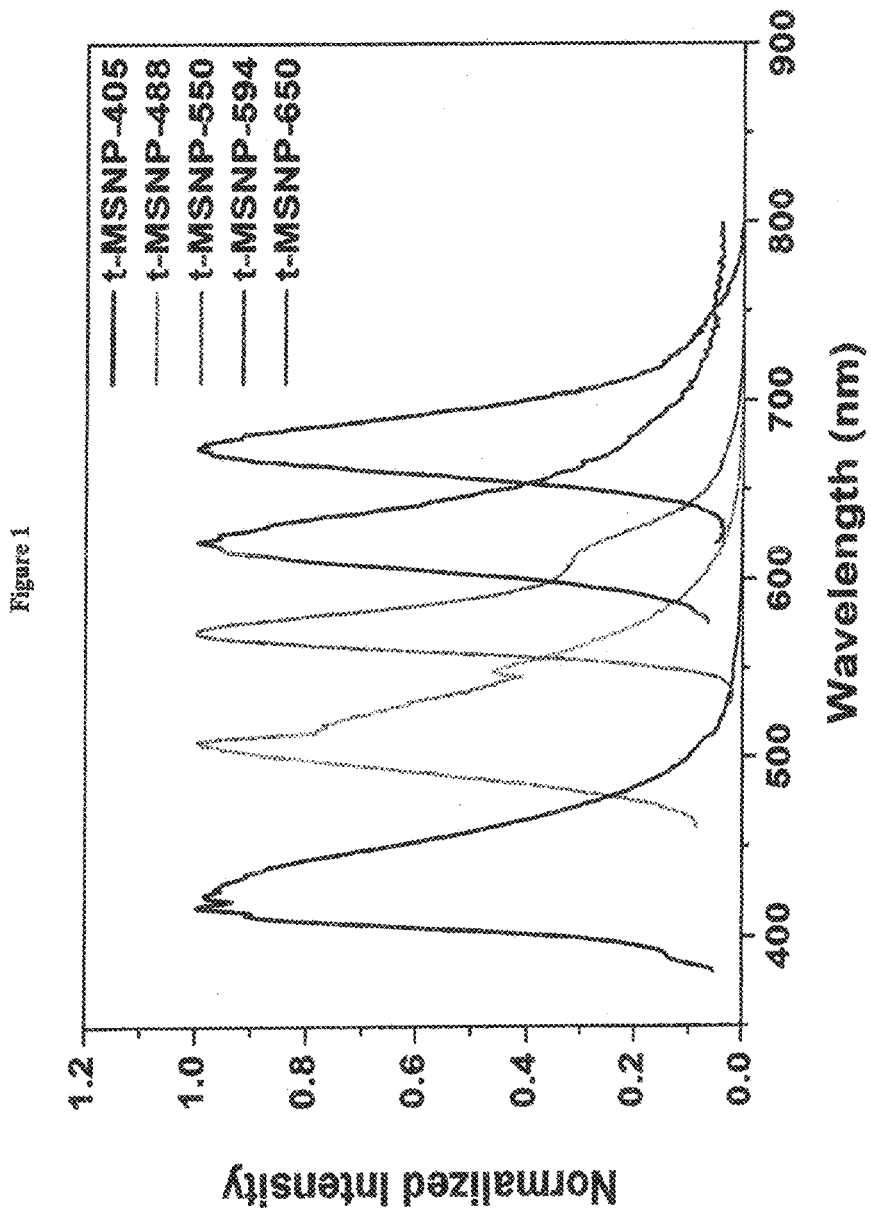
FIG. 1 (S1) shows the photoluminescence spectra of surfactant-free of large e-MSNPs covalently labeled with DyLight 405, 488, 550, 594, or 650 dyes: (a) large e-MSNP and (B) large TMSNP as determined in the experiment(s) of Example 2.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diastéromers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein.

The term "cargo" is used herein to describe any molecule or compound, whether a small molecule or macromolecule having an activity relevant to its use in TMSNPs, especially including biological activity, which can be included in TMSNPs according to the present invention. The cargo may be included within the pores and/or on the surface of the TMSNP according to the present invention. Representative cargo may include, for example, a small molecule bioactive agent, a nucleic acid (e.g. RNA or DNA), a polypeptide, including a protein or a carbohydrate "or a transmembrane receptor". Particular examples of such cargo include RNA, such as mRNA, siRNA, shRNA micro RNA, a polypeptide or protein, including a protein toxin (e.g. ricin toxin A-chain or diphtheria toxin A-chain) and/or DNA (including double stranded or linear DNA, complementary DNA (cDNA), minicircle DNA, naked DNA and plasmid DNA which optionally may be supercoiled and/or packaged (e.g. with histones) and which may be optionally modified with a nuclear localization sequence). Cargo may also include a reporter as described herein.

The term "mesoporous silica nanoparticles" (MSNPs) is used to describe a silica nanoparticles containing pores.

A nanoparticle may have a variety of shapes and cross-sectional geometries that may depend, in part, upon the process used to produce the particles. In one embodiment, a nanoparticle may have a shape that is a torus (torroidal), which is the preferred embodiment of the present invention. A nanoparticle may include particles having two or more of the aforementioned shapes. In one embodiment, a cross-sectional geometry of the particle may be one or more of torroidal, circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles.

The phrase "effective average particle size" as used herein to describe a multiparticulate (e.g., a porous nanoparticulate) means that at least 50% of the particles therein are of a specified size. Accordingly, "effective average particle size of less than about 2,000 nm in diameter" means that at least 50% of the particles therein are less than about 2000 nm in diameter. In certain embodiments, nanoparticulates have an effective average particle size of less than about 2,000 nm (i.e., 2 microns), less than about 1,900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, less than about 50 nm, less than 30 nm, less than 25 nm, less than 20 nm, less than 15 nm, less than 10 nm, as measured by light-scattering methods, microscopy, or other appropriate methods. "$D_{50}$" refers to the particle size below which 50% of the particles in a multiparticulate fall. Similarly, "$D_{90}$" is the particle size below which 90% of the particles in a multiparticulate fall.

The TMSNP size distribution, according to the present invention, depends on the application, but is principally monodisperse (e.g., a uniform sized population varying no more than about 5-20% in diameter, as otherwise described herein). The term "monodisperse" is used as a standard definition established by the National Institute of Standards and Technology (NIST) (*Particle Size Characterization*, Special Publication 960-1, January 2001) to describe a distribution of particle size within a population of particles, in this case nanoparticles, which particle distribution may be considered monodisperse if at least 90% of the distribution lies within 5% of the median size. See Takeuchi, et al., *Advanced Materials*, 2005, 17, No. 8, 1067-1072.

In certain embodiments, mesoporous silica nanoparticles can be range, e.g., from around 5 nm to around 500 nm (preferably about 50 nm to about 500 nm) in size, including all integers and ranges there between. The size is measured as the longest axis of the particle. In various embodiments, the particles are from around 10 nm to around 500 nm and from around 10 nm to around 100 nm in size. The mesoporous silica nanoparticles have a porous structure. The pores can be from around 1 to around 20 nm in diameter, including all integers and ranges there between. In one embodiment, the pores are from around 1 to around 10 nm in diameter. In one embodiment, around 90% of the pores are from around 1 to around 20 nm in diameter. In another embodiment, around 95% of the pores are around 1 to around 20 nm in diameter.

Preferred TMSNPs according to the present invention: are monodisperse and range in size from about 25 nm to about 300 nm; exhibit stability (colloidal stability); have single cell binding specification to the substantial exclusion of non-targeted cells; are neutral or cationic for specific targeting (preferably cationic); are optionally modified with agents such as PEI, NMe3+, dye, crosslinker, ligands (ligands provide neutral charge); and optionally, are used in combination with a cargo to be delivered to a targeted cell.

In certain embodiments, the TMSNPs are monodisperse and range in size from about 25 nm to about 300 nm. The sizes used preferably include 50 nm (+/−10 nm) and 150 nm (+/−15 nm), within a narrow mondisperse range, but may be more narrow in range. A broad range of particles is not used because such a population is difficult to control and to target specifically.

The term "torroidal" is used to describe the shape of the MSNPs of the present invention. A torroidal nanoparticle as defined herein is a nanoparticle (whether spherical, elliptical or having a similar three dimensional structure) which has a central pore similar to a donut as well as additional pores. Torroidal MSNPs according to the present invention, in addition to having a central pore, also contains at least two additional pores which may vary in size/diameter as otherwise described herein.

The term "PEGylated" in its principal use refers to an MSNP which has been produced using PEG-containing silanes or zwitterionic group-containing silanes to form the MSNP. In general, the amount of the PEG-containing silanes and/or zwitterionic-containing silanes which optionally are used to produce MSNPs according to the present invention represent about 0.05% to about 50% (about 0.1% to about 35%, about 0.5% to about 25%, about 1% to about 20%, about 2.5% to about 30%, about 0.25% to about 10%, about 0.75% to about 15%) by weight of these monomers in combination with the silane monomers which are typically used to form MSNPs. A PEG-containing silane is any silane which contains a PEG as one of the substituents and the remaining groups can facilitate the silane reacting with other silanes to produce MSNPs according to the present invention. Preferred PEG-containing silanes and/or zwitterionic-containing silanes which are used in the present invention to create PEGylated MSNPs include 2-[methoxy(polyethyleneoxy)propyl]trimethoxysilane (containing varying molecular weights of PEG ranging from about 100 to 10,000 average molecule weight, often about 200 to 5,000 average molecular weight, about 1,000-2,500 average molecular weight, about 1500-2000 average molecular weight) and 3-{[Dimethoxyl(3-trimethoxysilyl)propyl]ammonio)pro-pane-1-sulfonate and mixtures thereof, among others. The term "PEGylated" may also refer to lipid bilayers which contain a portion of lipids which are PEGylated (from about 0.02% up to about 50%, about 0.1% to about 35%, about 0.5% to about 25%, about 1% to about 15%, about 0.5% to about 7.5%, about 1% to about 12.5% by weight of the lipids used to form the lipid bilayer or multilayer). These lipids often are amine-containing lipids (e.g DOPE and DPPE)

which are conjugated or derivatized to contain a PEG group (having an average molecule weight ranging from about 100 to 10,000, about 200 to 5,000, about 1,000-5,000, including 1,000, 2000, 3000 and 3400) and combined with other lipids to form the bilayer/multilayer which encapsulates the MSNP.

The terms "targeting ligand" and "targeting active species" are used to describe a compound or moiety (preferably an antigen) which is complexed or preferably covalently bonded to the surface of a TMSNPs and/or protocells according to the present invention which binds to a moiety on the surface of a cell to be targeted so that the TMSNPs and/or protocells may selectively bind to the surface of the targeted cell and deposit their contents into the cell. The targeting active species for use in the present invention is preferably a targeting peptide as otherwise described herein, a polypeptide including an antibody or antibody fragment, an aptamer, or a carbohydrate, among other species which bind to a targeted cell.

Preferred ligands which may be used to target cells include peptides, affibodies and antibodies (including monoclonal and/or polyclonal antibodies). In certain embodiments, targeting ligands selected from the group consisting of Fcγ from human IgG (which binds to Fcγ receptors on macrophages and dendritic cells), human complement C3 (which binds to CR1 on macrophages and dendritic cells), ephrin B2 (which binds to EphB4 receptors on alveolar type II epithelial cells), and the SP94 peptide (which binds to unknown receptor(s) on hepatocyte-derived cells). Targeting ligands in certain aspects of the invention target T-Cell for therapy.

The charge is controlled based on what is to be accomplished (via PEI, NMe3+, dye, crosslinker, ligands, etc.), but for targeting the charge is preferably cationic. Charge also changes throughout the process of formation. Initially the targeted particles are cationic and are often delivered as cationically charged nanoparticles, however post modification with ligands they are closer to neutral. The ligands which find use in the present invention include peptides, affibodies and antibodies, among others. These ligands are site specific and are useful for targeting specific cells which express peptides to which the ligand may bind selectively to targeted cells.

TMSNPs pursuant to the present invention may be used to deliver cargo to a targeted cell, including, for example, cargo component selected from the group consisting of at least one polynucleotide, such as double stranded linear DNA, minicircle DNA, naked DNA or plasmid DNA, messenger RNA, small interfering RNA, small hairpin RNA, microRNA, a polypeptide, a protein, a drug (in particular, an anticancer drug such as a chemotherapeutic agent), an imaging agent, or a mixture thereof. The MSNPs pursuant to the present invention are effective for accommodating cargo which are long and thin (e.g. naked) in three-dimensional structure, such as polynucleotides (e.g. various DNA and RNA) and polypeptides.

In protocells of the invention, a PEGylated lipid bi- or multilayer encapsulates a population of MSNPs as described herein and comprises (1) a PEGylated lipid which is optionally-thiolated (2) at least one additional lipid and, optionally (3) at least one targeting ligand which is conjugated to the outer surface of the lipid bi- or multilayer and which is specific against one or more receptors of white blood cells and arterial, venous and/or capillary vessels or combinations thereof, or which is specific against one or more receptors of targets a cancer cell, a bacterium, or a virus.

Protocells of the invention are highly flexible and modular. High concentrations of physiochemically-disparate molecules can be loaded into the protocells and their therapeutic and/or diagnostic agent release rates can be optimized without altering the protocell's size, size distribution, stability, or synthesis strategy. Properties of the supported lipid bi- or multilayer and mesoporous silica nanoparticle core can also be modulated independently, thereby optimizing properties as surface charge, colloidal stability, and targeting specificity independently from overall size, type of cargo(s), loading capacity, and release rate.

The terms "treat", "treating", and "treatment", are used synonymously to refer to any action providing a benefit to a patient at risk for or afflicted with a disease, including improvement in the condition through lessening, inhibition, suppression or elimination of at least one symptom, delay in progression of the disease, prevention, delay in or inhibition of the likelihood of the onset of the disease, etc. In the case of viral infections, these terms also apply to viral infections and preferably include, in certain particularly favorable embodiments the eradication or elimination (as provided by limits of diagnostics) of the virus which is the causative agent of the infection.

The term "pharmaceutically acceptable" as used herein means that the compound or composition is suitable for administration to a subject, including a human patient, to achieve the treatments described herein, without unduly deleterious side effects in light of the severity of the disease and necessity of the treatment.

Treatment, as used herein, encompasses both prophylactic and therapeutic treatment, principally of cancer, but also of other disease states, including bacterial and viral infections, (e.g. HBV and/or HCV). Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease (inhibition) that subsequently occurs, especially including metastasis of cancer. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present invention is effective to decrease the severity of the disease or lengthen the lifespan of the mammal so afflicted, as in the case of cancer, or inhibit or even eliminate the causative agent of the disease, as in the case of hepatitis B virus (HBV) and/or hepatitis C virus infections (HCV) infections.

Our novel TMSNPs and protocells can also be used to treat a wide variety of bacterial infections including, but not limited to, infections caused by bacteria selected from the group consisting of *F. tularensis, B. pseudomallei, Mycobacterium, staphylococcus, streptococcaceae, neisseriaaceae, cocci, enterobacteriaceae, pseudomonadaceae, vibrionaceae, campylobacter, pasteurellaceae, bordetella, francisella, brucella, legionellaceae, bacteroidaceae,* gram-negative bacilli, *clostridium, corynebacterium, propionibacterium,* gram-positive bacilli, anthrax, *actinomyces, nocardia, mycobacterium, treponema, borrelia, leptospira, mycoplasma, ureaplasma, rickettsia, chlamydiae* and *P. aeruginosa.*

Antibiotic TMSNPs and protocells of the invention can contain one or more antibiotics, e.g. "Antibiotics" include, but are not limited to, compositions selected from the group consisting of Gentamicin, Kanamycin, Neomycin, Netilmicin, Tobramycin, Paromomycin, Spectinomycin, Geldanamycin, Herbimycin, Rifaximin, Streptomycin, Ertapenem, Doripenem, Imipenem/Cilastatin, Meropenem, Cefadroxil, Cefazolin, Cephalothin, Cephalexin, Cefaclor, Cefamandole, Cefoxitin, Cefprozil, Cefuroxime, Cefixime, Cefdinir, Cefditoren, Cefoperazone Cefotaxime, Cefpodoxime, Ceftazadime, Ceftibuten, Ceftizoxime Ceftriaxone, Cefepime, Ceftaroline fosamil, Ceftobiprole, Teicoplanin, Vancomycin, Telavancin, Daptomycin, Oritavancin, WAP-8294A, Azithromycin, Clarithromycin, Dirithromycin, Erythromycin, Roxithromycin, Telithromycin, Spiramycin, Clindamycin, Lincomycin, Aztreonam, Furazolidone, Nitrofurantoin, Oxazolidonones, Linezolid, Posizolid, Radezolid, Torezolid, Amoxicillin, Ampicillin, Azlocillin, Carbenicillin, Cloxacillin Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Mafenide, Sulfacetamide, Sulfadiazine, Sulfadimethoxine, Sulfamethizole, Sulfamethoxazole, Sulfasalazine, Sulfisoxazole, Trimethoprim-Sulfamethoxazole, Sulfonamidochrysoidine, Demeclocycline, Doxycycline, Vibramycin Minocycline, Tigecycline, Oxytetracycline, Tetracycline, Clofazimine, Capreomycin, Cycloserine, Ethambutol, Rifampicin, Rifabutin, Rifapentine, Arsphenamine, Chloramphenicol, Fosfomycin, Fusidic acid, Metronidazole, Mupirocin, Platensimycin, Quinupristin/Dalfopristin, Thiamphenicol, Tigecycline and Tinidazole and combinations thereof.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

The term "additional anticancer agent" shall mean chemotherapeutic agents such as an agent selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes. These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatinib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6,Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

TMSNPs and protocells of the invention can comprise anti-cancer agents selected from the group consisting of doxorubicin-loaded liposomes that are functionalized by polyethylene glycol (PEG), antimetabolites, inhibitors of topoisomerase I and II, alkylating agents and microtubule inhibitors, adriamycin aldesleukin; alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustard; valrubicin; valtorcitabine (monoval LDC); vinblastine; vinorelbine; zoledronate; and mixtures thereof.

In certain embodiments, TMSNPs and protocells of the invention comprise anti-cancer drugs selected from the group consisting of doxorubicin, melphalan, bevacizumab, dactinomycin, cyclophosphamide, doxorubicin liposomal, amifostine, etoposide, gemcitabine, altretamine, topotecan, cyclophosphamide, paditaxel, carboplatin, cisplatin, and taxol.

TMSNPs and protocells of the invention can include one or more antiviral agents to treat viral infections, especially including HIV infections, HBV infections and/or HCV infections. Exemplary anti-HIV agents include, for example, nucleoside reverse transcriptase inhibitors (NRTI), nonnucloeoside reverse transcriptase inhibitors (NNRTI), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Anti-HCV agents include, for example, interferon, pegylated intergeron, ribavirin, NM 283, VX-950 (telaprevir), SCH 50304, TMC435, VX-500, BX-813, SCHSO3034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

TMSNPs and protocells of the invention can also be used to diagnose and treat a "vascular disorder". A "vascular disorder" includes but is not limited to ischemic stroke, hemorrhagic stroke, transient ischemic attack (TIA), vascular inflammation due to meningitis, atherosclerosis, thrombi or emboli resulting from atherosclerosis, arteritis, physical obstruction of arterial blood supply to the brain, lacunar stroke, hypoperfusion embodying diffuse injury caused by non-localized cerebral ischemia, myocardial infarction and arrhythmia, restenosis associated with percutaneous transluminal coronary angioplasty, peripheral vascular disease and cerebral vascular disease, venous occlusive disorders such as deep vein thrombosis, and hypercoagulopathies. Vascular disease treatments include but are not limited to treatment of peripheral artery diseases (e.g. with cholesterol-lowering medications, high blood pressure medications, medication to control blood sugar, medications to prevent blood clots, symptom-relief medications, angioplasty and surgery, thrombolytic therapy and supervised exercise programs), cerebrovascular disorder treatments (e.g. aspirin, TPA, mechanical clot removal, carotid endarterectomy, angioplasty and stents), treatment of atherosclerosis (e.g. cholesterol medications, anti-platelet medications, beta blocker medications, angiotensin-converting enzyme (ACE) inhibitors, calcium channel blockers, water pills (diuretics), angioplasty, endarterectomy, thrombolytic therapy, and bypass surgery).

Typically the TMSNPs and protocells according to the present invention are loaded with cargo to a capacity up to about 50 weight % or more (from about 0.01% to about 50%, about 0.02% to about 40%, about 0.2 to about 35%, about 0.5% to about 25%, about 1% to about 25%, about 1.5% to about 15%, about 0.1% to about 10%, about 0.01% to about 5%): defined as (cargo weight/weight of loaded protocell)×100. The optimal loading of cargo is often about 0.01 to 10% but this depends on the drug or drug combination which is incorporated as cargo into the MSNPs. This is generally expressed in μM per $10^{10}$ particles where we have values ranging from 2000-100 μM per $10^{10}$ particles. Preferred MSNPs according to the present invention exhibit release of cargo at pH about 5.5, which is that of the endosome, but are stable at physiological pH of 7 or higher (7.4).

The surface area of the internal space for loading is the pore volume whose optimal value ranges from about 1.1 to 0.5 cubic centimeters per gram (cc/g). Note that in the TMSNPs according to one embodiment of the present invention, the surface area is mainly internal as opposed to the external geometric surface area of the nanoparticle.

The term "lipid" is used to describe the components which are used to form lipid bi- or multilayers on the surface of the nanoparticles which are used in the present invention and may include a PEGylated lipid. Various embodiments provide nanostructures which are constructed from nanoparticles which support a lipid bilayer(s). In embodiments according to the present invention, the nanostructures preferably include, for example, a core-shell structure including a porous particle core surrounded by a shell of lipid bilayer (s). The nanostructure, preferably a porous alum nanostructure as described above, supports the lipid bilayer membrane structure.

The lipid bi- or multilayer supported on the porous particle according to one embodiment of the present invention has a lower melting transition temperature, i.e. is more fluid than a lipid bi- or multilayer supported on a non-porous support or the lipid bi- or multilayer in a liposome. This is sometimes important in achieving high affinity binding of immunogenic peptides or targeting ligands at low peptide densities, as it is the bilayer fluidity that allows lateral diffusion and recruitment of peptides by target cell surface receptors. One embodiment provides for peptides to cluster, which facilitates binding to a complementary target.

In the present invention, the lipid bi- or multilayer may vary significantly in composition. Ordinarily, any lipid or polymer which may be used in liposomes may also be used in TMSNPs according to the present invention. Preferred lipids are as otherwise described herein.

In embodiments according to the invention, the lipid bi- or multilayer of the protocells can provide biocompatibility and can be modified to possess targeting species including, for example, antigens, targeting peptides, fusogenic peptides, antibodies, aptamers, and PEG (polyethylene glycol) to allow, for example, further stability of the protocells and/or a targeted delivery into a cell to maximize an immunogenic response. PEG, when included in lipid bilayers, can vary widely in molecular weight (although PEG ranging from about 10 to about 100 units of ethylene glycol, about 15 to about 50 units, about 15 to about 20 units, about 15 to about 25 units, about 16 to about 18 units, etc, may be used) and the PEG component which is generally conjugated to phospholipid through an amine group comprises about 1% to about 20%, preferably about 5% to about 15%, about 10% by weight of the lipids which are included in the lipid bi- or multilayer. The PEG component is generally conjugated to an amine-containing lipid such as DOPE or DPPE or other lipid, but in alternative embodiments may also be incorporated into the MSNPs, through inclusion of a PEG containing silane.

Numerous lipids which are used in liposome delivery systems may be used to form the lipid bi- or multilayer on nanoparticles to provide MANPS according to the present invention. Virtually any lipid which is used to form a liposome may be used in the lipid bi- or multilayer which surrounds the nanoparticles to form MANPS according to an embodiment of the present invention. Preferred lipids for use in the present invention include, for example, 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino] lauroyl]-sn-Glycero-3-Phosphocholine (18:1-12:0 NBD PC), 1-palmitoyl-2-{12-[(7-nitro-2-1,3-benzoxadiazol-4-yl) amino]lauroyl}-sn-glycero-3-phosphocholine (16:0-12:0 NBD PC), cholesterol and mixtures/combinations thereof. Cholesterol, not technically a lipid, but presented as a lipid for purposes of an embodiment of the present invention given the fact that cholesterol may be an important component of the lipid bilayer of protocells according to an embodiment of the invention. Often cholesterol is incorporated into lipid bilayers of protocells in order to enhance structural integrity of the bilayer. These lipids are all readily available commercially from Avanti Polar Lipids, Inc. (Alabaster, Ala., USA). DOPE and DPPE are particularly useful for conjugating (through an appropriate crosslinker) PEG, peptides, polypeptides, including immunogenic peptides, proteins and antibodies, RNA and DNA through the amine group on the lipid.

TMSNPs and protocells of the invention can be PEGylated with a variety of polyethylene glycol-containing compositions as described herein. PEG molecules can have a variety of lengths and molecular weights and include, but are not limited to, PEG 200, PEG 1000, PEG 1500, PEG 4600, PEG 10,000, PEG-peptide conjugates or combinations thereof.

The term "reporter" is used to describe an imaging agent or moiety which is incorporated into the phospholipid bilayer or cargo of MANPS according to an embodiment of the present invention and provides a signal which can be measured. The moiety may provide a fluorescent signal or may be a radioisotope which allows radiation detection, among others. Exemplary fluorescent labels for use in MSNPs and protocells (preferably via conjugation or adsorption to the lipid bi- or multilayer or silica core, although these labels may also be incorporated into cargo elements such as DNA, RNA, polypeptides and small molecules which are delivered to cells by the protocells) include Hoechst 33342 (350/461), 4',6-diamidino-2-phenylindole (DAPI, 356/451), Alexa Fluor® 405 carboxylic acid, succinimidyl ester (401/421), CellTracker™ Violet BMQC (415/516), CellTracker™ Green CMFDA (492/517), calcein (495/515), Alexa Fluor® 488 conjugate of annexin V (495/519), Alexa Fluor® 488 goat anti-mouse IgG (H+L) (495/519), Click-iT® AHA Alexa Fluor® 488 Protein Synthesis HCS Assay (495/519), LIVE/DEAD® Fixable Green Dead Cell Stain Kit (495/519), SYTOX® Green nucleic acid stain (504/523), MitoSOX™ Red mitochondrial superoxide indicator (510/580). Alexa Fluor® 532 carboxylic acid, succinimidyl ester(532/554), pHrodo™ succinimidyl ester (558/576), CellTracker™ Red CMTPX (577/602), Texas Red® 1,2-dihexadecanoyl-sn-glycero-3-phosphoethanolamine (Texas Red® DHPE, 583/608), Alexa Fluor® 647 hydrazide (649/666), Alexa Fluor® 647 carboxylic acid, succinimidyl ester (650/668), Ulysis™ Alexa Fluor® 647 Nucleic Acid Labeling Kit (650/670) and Alexa Fluor® 647 conjugate of annexin V (650/665). Moities which enhance the fluorescent signal or slow the fluorescent fading may also be incorporated and include SlowFade® Gold antifade reagent (with and without DAPI) and Image-iT® FX signal enhancer. All of these are well known in the art.

Additional reporters include polypeptide reporters which may be expressed by plasmids (such as histone-packaged supercoiled DNA plasmids) and include polypeptide reporters such as fluorescent green protein and fluorescent red protein. Reporters pursuant to the present invention are utilized principally in diagnostic applications including diagnosing the existence or progression of cancer (cancer tissue) in a patient and or the progress of therapy in a patient or subject.

Pharmaceutical compositions according to the present invention comprise an effective population of TMSNPs and/or protocells as otherwise described herein formulated to effect an intended result (e.g. immunogenic result, therapeutic result and/or diagnostic analysis, including the monitoring of therapy) formulated in combination with a pharmaceutically acceptable carrier, additive or excipient. The TMSNPs and/or protocells within the population of the composition may be the same or different depending upon the desired result to be obtained. Pharmaceutical compositions according to the present invention may also comprise an addition bioactive agent or drug, such as an antibiotic or antiviral agent.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, intrathecal or intramuscular injection, among others, including buccal, rectal and transdermal administration. Subjects contemplated for treatment according to the method of the invention include humans, companion animals, laboratory animals, and the like. The invention contemplates immediate and/or sustained/controlled release compositions, including compositions which comprise both immediate and sustained release formulations. This is particularly true when different populations of MSNPs and/or protocells are used in the pharmaceutical compositions or when additional bioactive agent(s) are used in combination with one or more populations of protocells as otherwise described herein.

Formulations containing the compounds according to the present invention may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients.

An injectable composition for parenteral administration (e.g. intravenous, intramuscular or intrathecal) will typically contain the compound in a suitable i.v. solution, such as sterile physiological salt solution. The composition may also be formulated as a suspension in an aqueous emulsion.

Liquid compositions can be prepared by dissolving or dispersing the population of TMSNPs and/or protoells (about 0.5% to about 20% by weight or more), and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject according to the present invention.

Methods of treating patients or subjects in need for a particular disease state or infection comprise administration an effective amount of a pharmaceutical composition comprising therapeutic TMSNPs and/or protocells and optionally at least one additional bioactive (e.g. antiviral) agent according to the present invention.

Diagnostic methods according to the present invention comprise administering to a patient in need an effective amount of a population of diagnostic TMSNPs and/or protocells (e.g., TMSNPs and/or protocells which comprise a target species, such as a targeting peptide which binds selectively to cancer cells and a reporter component to indicate the binding of the protocells) whereupon the binding of the TMSNPs and/or protocells to cells as evidenced by the reporter component (moiety) will enable a diagnosis of the existence of a disease state in the patient.

An alternative of the diagnostic method of the present invention can be used to monitor the therapy of a disease state in a patient, the method comprising administering an effective population of diagnostic TMSNPs and/or protocells (e.g., TMSNPs and/or protocells which comprise a target species, such as a targeting peptide which binds selectively to target cells and a reporter component to indicate the binding of the protocells to cancer cells if the cancer cells are present) to a patient or subject prior to treatment, determining the level of binding of diagnostic protocells to target cells in said patient and during and/or after therapy, determining the level of binding of diagnostic protocells to target cells in said patient, whereupon the difference in binding before the start of therapy in the patient and during and/or after therapy will evidence the effectiveness of therapy in the patient, including whether the patient has completed therapy or whether the disease state has been inhibited or eliminated.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

The term "histone-packaged supercoiled plasmid DNA" is used to describe a preferred component of protocells according to the present invention which utilize a preferred plasmid DNA which has been "supercoiled" (i.e., folded in on itself using a supersaturated salt solution or other ionic solution which causes the plasmid to fold in on itself and "supercoil" in order to become more dense for efficient packaging into the protocells). The plasmid may be virtually any plasmid which expresses any number of polypeptides or encode RNA, including small hairpin RNA/shRNA or small interfering RNA/siRNA, as otherwise described herein. Once supercoiled, (using the concentrated salt or other anionic solution), the supercoiled plasmid DNA is then complexed with histone proteins to produce a histone-packaged "complexed" supercoiled plasmid DNA.

"Packaged" DNA herein refers to DNA that is loaded into protocells (either adsorbed into the pores or confined directly within the nanoporous silica core itself). To minimize the DNA spatially, it is often packaged, which can be accomplished in several different ways, from adjusting the charge of the surrounding medium to creation of small complexes of the DNA with, for example, lipids, proteins, or other nanoparticles (usually, although not exclusively cationic). Packaged DNA is often achieved via lipoplexes (i.e. complexing DNA with cationic lipid mixtures). In addition, DNA has also been packaged with cationic proteins (including proteins other than histones), as well as gold nanoparticles (e.g. NanoFlares—an engineered DNA and metal complex in which the core of the nanoparticle is gold).

Any number of histone proteins, as well as other means to package the DNA into a smaller volume such as normally cationic nanoparticles, lipids, or proteins, may be used to package the supercoiled plasmid DNA "histone-packaged supercoiled plasmid DNA", but in therapeutic aspects which relate to treating human patients, the use of human histone proteins are preferably used. In certain aspects of the invention, a combination of human histone proteins H1, H2A, H2B, H3 and H4 in a preferred ratio of 1:2:2:2:2, although other histone proteins may be used in other, similar ratios, as is known in the art or may be readily practiced pursuant to the teachings of the present invention. The DNA may also be double stranded linear DNA, instead of plasmid DNA, which also may be optionally supercoiled and/or packaged with histones or other packaging components.

Other histone proteins which may be used in this aspect of the invention include, for example, H1F, H1F0, H1FNT, H1FOO, H1FX H1H1 HIST1H1A, HIST1H1B, HIST1H1C, HIST1H1D, HIST1H1E, HIST1H1T; H2AF, H2AFB1, H2AFB2, H2AFB3, H2AFJ, H2AFV, H2AFX, H2AFY, H2AFY2, H2AFZ, H2A1, HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, H2A2, HIST2H2AA3, HIST2H2AC, H2BF, H2BFM, HSBFS, HSBFWT, H2B1, HIST1H2BA, HIST1HSBB, HIST1HSBC, HIST1HSBD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, H2B2, HIST2H2BE, H3A1, HIST1H3A, HIST1H3B, HIST1H3C, HIST1H3D, HIST1H3E, HIST1H3F, HIST1H3G, HIST1H3H, HIST1H3I, HIST1H3J, H3A2, HIST2H3C, H3A3, HIST3H3, H41, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, H44 and HIST4H4.

The term "nuclear localization sequence" refers to a peptide sequence incorporated or otherwise crosslinked into histone proteins which comprise the histone-packaged supercoiled plasmid DNA. In certain embodiments, protocells according to the present invention may further comprise a plasmid (often a histone-packaged supercoiled plasmid DNA) which is modified (crosslinked) with a nuclear localization sequence (note that the histone proteins may be crosslinked with the nuclear localization sequence or the plasmid itself can be modified to express a nuclear localization sequence) which enhances the ability of the histone-packaged plasmid to penetrate the nucleus of a cell and deposit its contents there (to facilitate expression and ultimately cell death. These peptide sequences assist in carrying the histone-packaged plasmid DNA and the associated histones into the nucleus of a targeted cell whereupon the plasmid will express peptides and/or nucleotides as desired to deliver therapeutic and/or diagnostic molecules (polypeptide and/or nucleotide) into the nucleus of the targeted cell. Any number of crosslinking agents, well known in the art, may be used to covalently link a nuclear localization sequence to a histone protein (often at a lysine group or other group which has a nucleophilic or electrophilic group in the side chain of the amino acid exposed pendant to the polypeptide) which can be used to introduce the histone packaged plasmid into the nucleus of a cell. Alternatively, a nucleotide sequence which expresses the nuclear localization sequence can be positioned in a plasmid in proximity to that which expresses histone protein such that the expression of the histone protein conjugated to the nuclear localization sequence will occur thus facilitating transfer of a plasmid into the nucleus of a targeted cell.

Proteins gain entry into the nucleus through the nuclear envelope. The nuclear envelope consists of concentric membranes, the outer and inner membrane. These are the gateways to the nucleus. The envelope consists of pores or large nuclear complexes. A protein translated with a NLS will bind strongly to importin (aka karyopherin), and together, the complex will move through the nuclear pore. Any number of nuclear localization sequences may be used to introduce histone-packaged plasmid DNA into the nucleus of a cell. Preferred nuclear localization sequences include $H_2N$-GNQSSNFGPMKGGNFGGRSSGPYGGGGQY-FAKPRNQGGYGGC-COOH (SEQ ID NO:1), RRMKWKK (SEQ ID NO:2), PKKKRKV (SEQ ID NO:3), and KR[PAATKKAGQA]KKKK (SEQ ID NO:4), the NLS of nucleoplasmin, a prototypical bipartite signal comprising two clusters of basic amino acids, separated by a spacer of about 10 amino acids. Numerous other nuclear localization sequences are well known in the art. See, for example, LaCasse, et al., *Nuclear localization signals overlap DNA- or RNA-binding domains in nucleic acid-binding proteins. Nucl., Acids Res.*, 23, 16-17-1656 1995); Weis, K. *Improtins and exportins: how to get in and out of the nucleus* [published erratum appears in Trends Biochem Sci 1998 Jul;23 (7):235]. TIBS, 23, 185-9 (1998); and Murat Cokol, Raj Nair & Burkhard Rost, "Finding nuclear localization signals", at the website ubic.bioc.columbia.edulpapers/2000 nls/paper.html#tab2.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A nucleic acid molecule is "operatively linked" to, or "operably associated with", an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The invention is described further in the following non-limiting examples.

EXAMPLE 1

Synthesis of Torus-shaped MSNPs According to the Present Invention

First, 0.4-1.2 mmole of CTAB was added to 150 mL of 0.5-2.0 M ammonium hydroxide solution in a 250 mL beaker. The mixture solution was placed and stirred (300 rpm) in an oil bath with a temperature controlled at 40° C. After 1 h, 0.88 M of dilute TEOS (prepared in ethanol) was added to the CTAB-ammonium hydroxide mixture solution under more vigorous stirring (600 rpm). After another 1 h stirring, the as-synthesized particle solution was aged without cover for 10-20 h at 30-50° C. in a static condition. Then, the as-synthesized oblate shaped mesoporous silica particle solution (~50 mL) was purified by ethanolic ammonia nitrate and ethanolic hydrochloric acid solutions. To obtain the torus shape mesoporous silica particles, the as-synthesized oblate shaped mesoporous silica particle solution was transferred to a Pyrex® media storage bottles and heated to 80-150° C. for 6-48 h. The further procedure to remove surfactant from particles followed the previously described method. The purified particles were suspended in absolute ethanol and stored at room temperature. Powdered samples were obtained by drying particles in ethanol using a rotary evaporator.

EXAMPLE 2

Hydrothermally Induced Morphological Transformation of Mesoporous Silica Nanoparticles: Ellipsoid to Torus Experimental Section
1. Materials.
All chemicals and reagents were used as received. Ammonium nitrate ($NH_4NO_3$), 3-aminopropyltriethoxysilane (98%, APTES), benyldimethylhexadecylammonium chloride (BDHAC), n-cetyltrimethylammonium bromide (CTAB), anhydrous N,N-dimethyl formamide (DMF), and tetraethyl orthosilicate (TEOS) were purchased from Sigma-Aldrich (St. Louis, Mo.). Ammonium hydroxide (NH$_4$OH, 28-30%) was obtained from VWR (West Chester, Pa.). Hydrochloric acid (36.5-38%, HCl) was purchased from EMD Chemicals (Gibbstown, N.J.). Absolute ethanol (EtOH) was obtained from Pharco-Aaper (Brookfield, Conn.). Heat inactivated fetal bovine serum (FBS), Trypsin-EDTA, and penicillin streptomycin (PS) were obtained from Gibco (Logan, Utah). Dulbecco's Modified Eagle's Medium (DMEM) with 4.5 g/L glucose, 110 μg/mL sodium pyruvate, 4.00 mM L-glutamine, and phenol red were purchased from CORNING celigro (Manassas, Va.). DyLight amine-reactive dyes, 405, 488, 550, 594, and 650 containing N-hydroxysuccinimide (NHS) esters were purchased from Thermo Scientific (Rockford, Ill.). 1, 2-dioleoyl-sn-glycero-3-phosphocholine (DOPC), 1, 2-distearoyl-snglycero-3-phosphocholine (DSPC), 1,2-distearoyl-sn-glycero-3-phosphoethanolamine-N-[methoxy(polyethylene glycol)-2000] (DSPE-PEG), phospholipids and cholesterol (Chol, ovine wool, >98%) were purchased from Avanti Polar Lipids (Birmingham, Ala.). DSPE-PEG-folic acid was obtained from NANOCS (New York, N.Y.).

2. Synthesis of Ellipsoid and Torus Shaped Mesoporous Silica Nanoparticles.

The ellipsoid shaped mesoporous silica nanoparticles (e-MSNPs) were prepared using an ammonia base-catalyzed method under a low surfactant condition.[1] First, 0.81 mmole of CTAB was added to 150 mL of 1.0 M NH$_4$OH solution in a 250 mL beaker. The mixture solution was placed and stirred (300 rpm) in an oil bath with a temperature controlled at 40° C. After 1 h, 4 mL of 0.88 M of dilute TEOS (prepared in ethanol) was added to the CTAB-ammonium hydroxide mixture solution under more vigorous stirring (600 rpm). After another 1 h stirring, the as-synthesized particle solution was aged without covering the top of beaker for 20 h at 40° C. in a static condition. To obtain the torus shaped mesoporous silica nanoparticles (t-MSNPs), the as-synthesized e-MSNP solution was transferred to a Pyrex® media storage bottles and heated to 120° C. in a conventional oven for 24 h. The further procedure to remove surfactant from particles followed a previously reported method.[1] The purified particles were suspended in absolute ethanol and stored at room temperature. Powdered samples were obtained by drying particles in ethanol under vacuum. For small t-MSNP synthesis, the concentration of NH$_4$OH and the amount of dilute TEOS were changed to 0.5 M and 3 mL, respectively. The other steps were followed by the previously described method. For DyLight Dye labeled e-MSNPs and t-MSNPs preparation, 1 mg of DyLight 405, 488, 550, 594, or 650 was dissolved in 0.5 mL of ethanol and then 0.5 mL of 4.25 mM APTES (in ethanol) was added. The DyLight dye-APTES mixture solution was covered with aluminium foil and kept in static conditions for at least 1 h. Similar to previously described steps, CTAB was dissovled in 1 M or 0.5 M NH$_4$OH soultion. Then, 1 mL of ethanolic DyLight dye-APTES solution and TEOS solution were mixed and added immediately to the CTAB NH$_4$OH solution under vigorous stirring. Again, the following steps were the same as the previously described method.

3. Liposome and Lipid Coated e-MSNP Preparation.

To prepare small and unilamellar vesicles (SUV), phospholipids (in chloroform) were mixed with cholesterol (6:3:1 DOPC/Chol/DSPE-PEG w/w ratio). Chloroform was removed under vacuum. Then, dried lipid film is hydrated in 0.5×PBS and sonicated in a warm water bath (~50° C., above the gel-liquid crystal transition temperature (Tc) of the lipid) for at least 30 min to obtain a clear liposome solution. Finally, the liposome solution was further passed through a 0.10 μm track-etched membrane (Whatman, Pscataway, N.J.) at least 21 times using a miniextruder (Avanti Polar Lipids, Birmingham, Ala.).

To form supported lipid bilayer on particles, 0.5 mL of 2 mg/mL e-MSNPs was added to 0.5 mL of prepared DOPC/Chol/DSPE-PEG liposome solution (1:2.5 w/w ratios). Mixture solution was kept in static conditions for at least 30 min. The excess non-fused liposomes are removed by two washes with 1×PBS using centrifugation (15000 g, 10 min). The lipid coated e-MSNPs were finally redispersed for further stability test, in vitro cell binding, and in vivo circulation experiments.

4. Cell Culture and Nanoparticle Uptake.

To study the nonspecific binding/uptake difference of bare e-MSNP, t-MSNPs, and lipid coated t-MSNPs to human endothelial cells (EA.hy926, ATCC-CRL-2922) and mouse macrophages (Raw 264. 7, ATCC-TIB-71), 5×10$^5$ of cells were seeded in 6-well plate. After 24 h, cells were incubated with 20 or 50 μg/mL of NPs in at 37° C. under 5% CO2 for 4 h. After NP exposure, cells were washed with PBS three times, removed by trypsin-EDTA, centrifuged, and then fixed in 1 mL of 3.7% formaldehyde PBS solution for 10 min). After fixation, cells were further washed with PBS one time and suspended in PBS before flow cytometry measurements.

5. Chicken Embryo Incubation and Particle Administration.

The ex ovo chicken embryo was prepared according to a published method.[2] Ex ovo chicken embryo experiments were conducted under UNM protocol #10-100652-T-HSC. Fertilized chicken eggs were purchased from East Mountain Hatchery (Edgewood, N. Mex.) and placed in an automated incubator (GQF 1500 professional, Savannah, Ga.) with controlled humid (70% RH) for 72-96 h at 40° C. Following incubation, egg shells were sterilized by brief immersion in ethanol and physically cleaned with a paper towel. Egg shells were then scored using a rotary tool and cracked into a sterilized weigh boat (VWR, West Chester, Pa.). Weigh boats were covered with a square plastic petri dish (VWR, West Chester, Pa.) and returned to the incubator until time of injection. For nanoparticle injections, 50 μL of bare or lipid coated t-MSNPs at 1 mg/mL were injected via a pulled glass capillary needle into the vein of the chorioallantoic membrane (CAM) and allowed to circulate for different periods of time. The embryo CAM vasculature was imaged using a customized avian embryo chamber and a Zeiss Axio Examiner (Dublin, Calif.) upright microscope with heated stage.

6. Characterization.

Transmission electron microscopy (TEM) images were taken on a JEOL 2010 (Tokyo, Japan) equipped with a Gatan Orius digital camera system (Warrendale, Pa.) under a 200 kV voltage. Scanning electron microscopy (SEM) images were taken on a Hitachi S-5200 Nano (Tokyo, Japan). Nitrogen adsorption-desorption isotherms of the extracted oblate and torus shaped mesoporous silica nanoparticles were obtained from on a Micromeritics ASAP 2020 (Norcross, Ga.) at 77 K. Samples were degassed at 120° C. for 12 h before measurements. The surface area and pore size was calculated following the Brunauer-Emmet-Teller (BET) equation in the range of P/P$_o$ from 0.05 to 0.1 and standard Barrett-Joyer-Halenda (BJH) method. Powdered X-ray diffraction (XRD) data was recorded on a Rigaku SmartLab X-ray diffractometer system (Tokyo, Japan). $^{29}$Si solid state MAS NMR spectra were acquired on a Bruker Avance III 600 (The Woodlands, Tex.) at 119.21 MHz. A 4 mm broadband MAS NMR probe, holding ~50 mg sample spinning at 4 kHz was used. The $^{29}$Si MAS NMR spectra were obtained using single pulse Bloch echo with a 240 s recycle delay for complete relaxation, while the variable amplitude (VACP) MAS NMR spectra were obtained with a 5 ms contact time, and a 5 s recycle delay. The $^{29}$Si chemical shifts were referenced to Q8M8 δ=+11.7 ppm with respect to TMS δ=0.0 ppm. Spectral deconvolutions were performed using the DMFIT software package. Photoluminescence spectra of DyLight labeled T-MSNPs were taken on a Photon Technology International QuantaMaster QM 40 spectrofluorometer (Birmingham, N.J.). Flow cytometry data were performed on a Becton-Dickinson FACScalibur flow cytometer (Sunnyvale, Calif.). Hydrodynamic size and zeta potential data were acquired on a Malvern Zetasizer Nano-ZS equipped with a He—Ne laser (633 nm) and Non-Invasive Backscatter optics (NIBS). All samples for dynamic light scattering (DLS) measurements were suspended in various media (DI, PBS, and DMEM+10% FBS) at 1 mg/mL. Measurements were carried out at 25° C. DLS measurements for each sample were obtained at least three runs. The hydrodynamic size of all samples was reported using z-average diameter. For zeta potential data, each sample was measured at least 100 runs and ensure the results meet quality criteria. All the reported values correspond to the average of at least three independent samples.

TABLE S1

Deconvolution of the direct $^{29}$Si MAS NMR spectra

| Samples | $Q^2$ | $Q^3$ | $Q^4$ | $(Q^2 + Q^3)/Q^4$ |
|---|---|---|---|---|
| Large e-MSNP | 4.0 | 58 | 38 | 1.63 |
| Large t-MSNP | 2.5 | 47 | 50.5 | 0.98 |

Further Examples and Results

Figure 2:
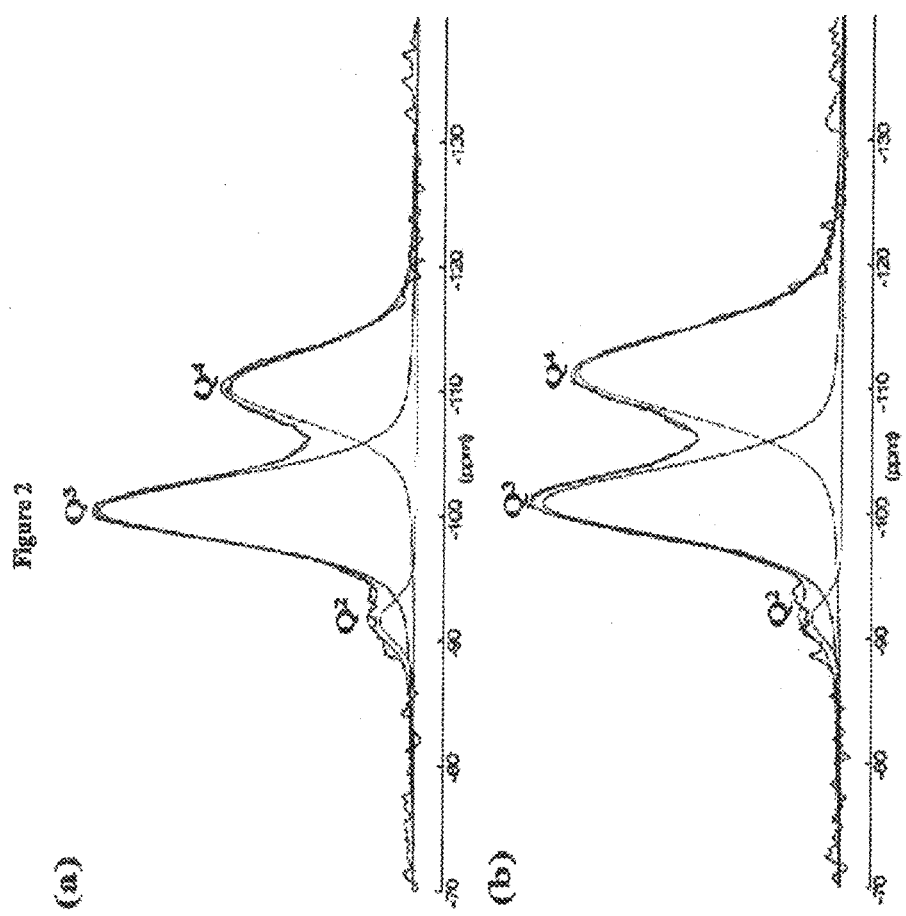
FIG. 2 (S2) shows $^{29}$Si solid-state MAS NMR spectra of extracted (a) large e-MSNP and (B) large TMSNP as determined in the experiment(s) of Example 2.
Figure 3:
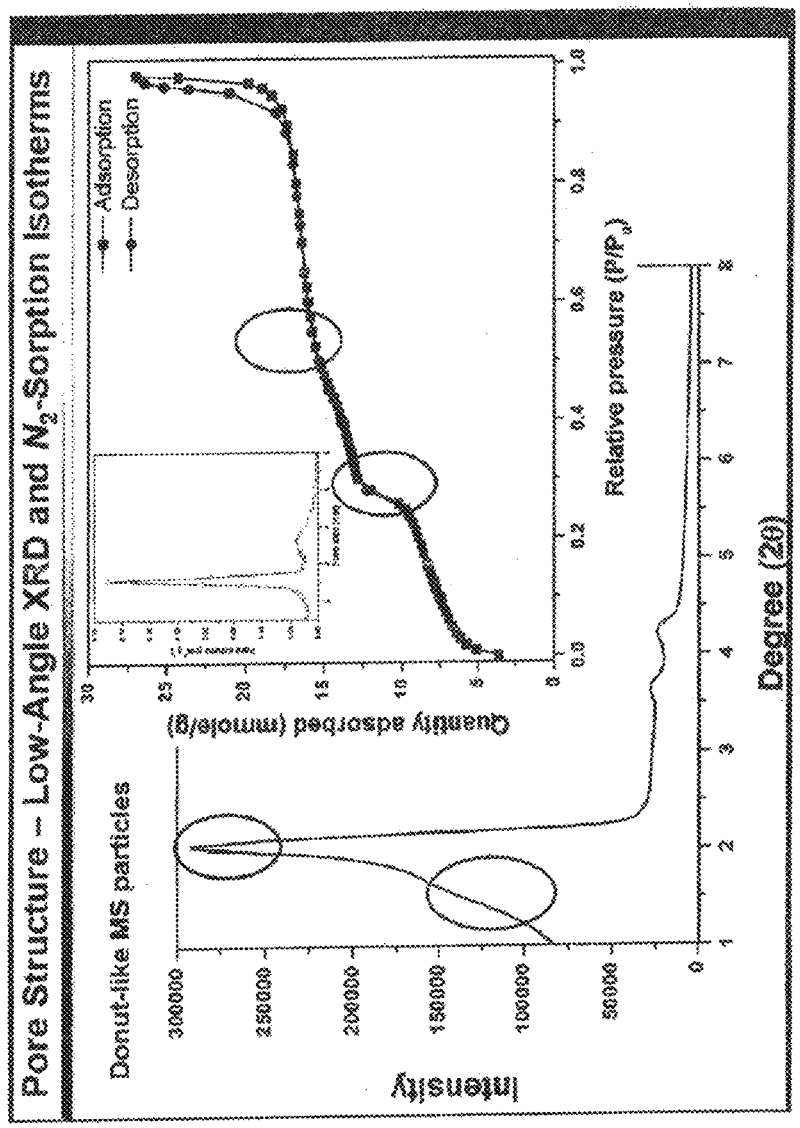
FIG. 3 shows pore structure data-low angle XRD and N2-sorption isotherms for TMSNPs made in accordance with the invention. As determined in the experiment(s) of Example 2.
Figure 4:
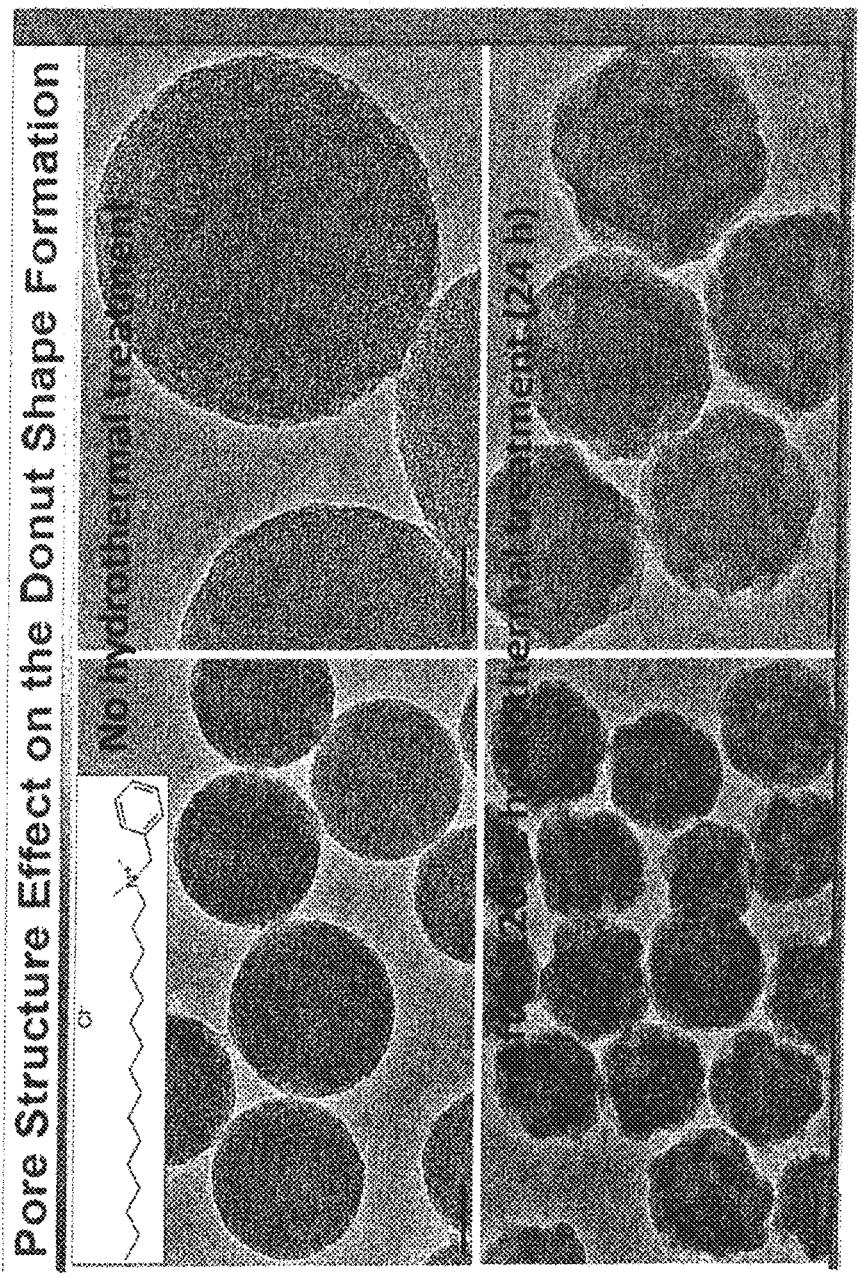
FIG. 4 shows the effect of pore structure on TMNSP formation. As determined in the experiment(s) of Example 2.
Figure 5:
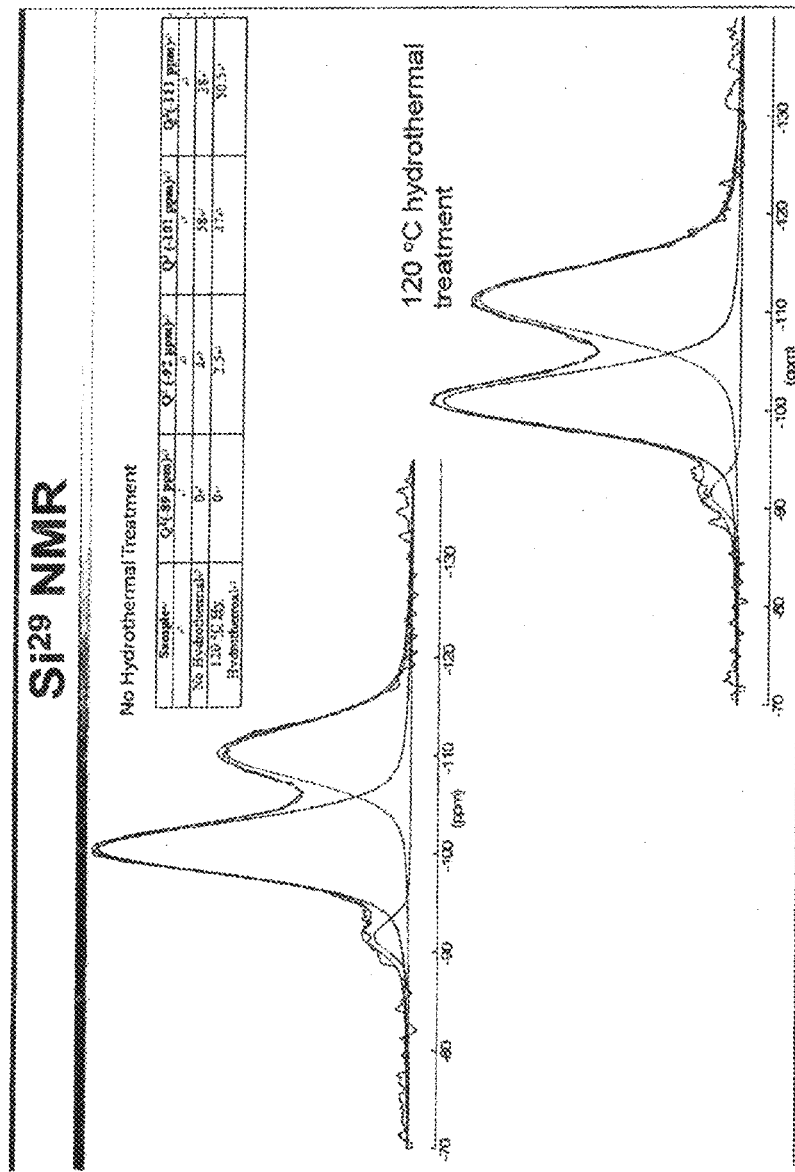
FIG. 5 shows $^{29}$Si data for TMSNPs made in accordance with the invention. As determined in the experiment(s) of Example 2.
Figure 7:
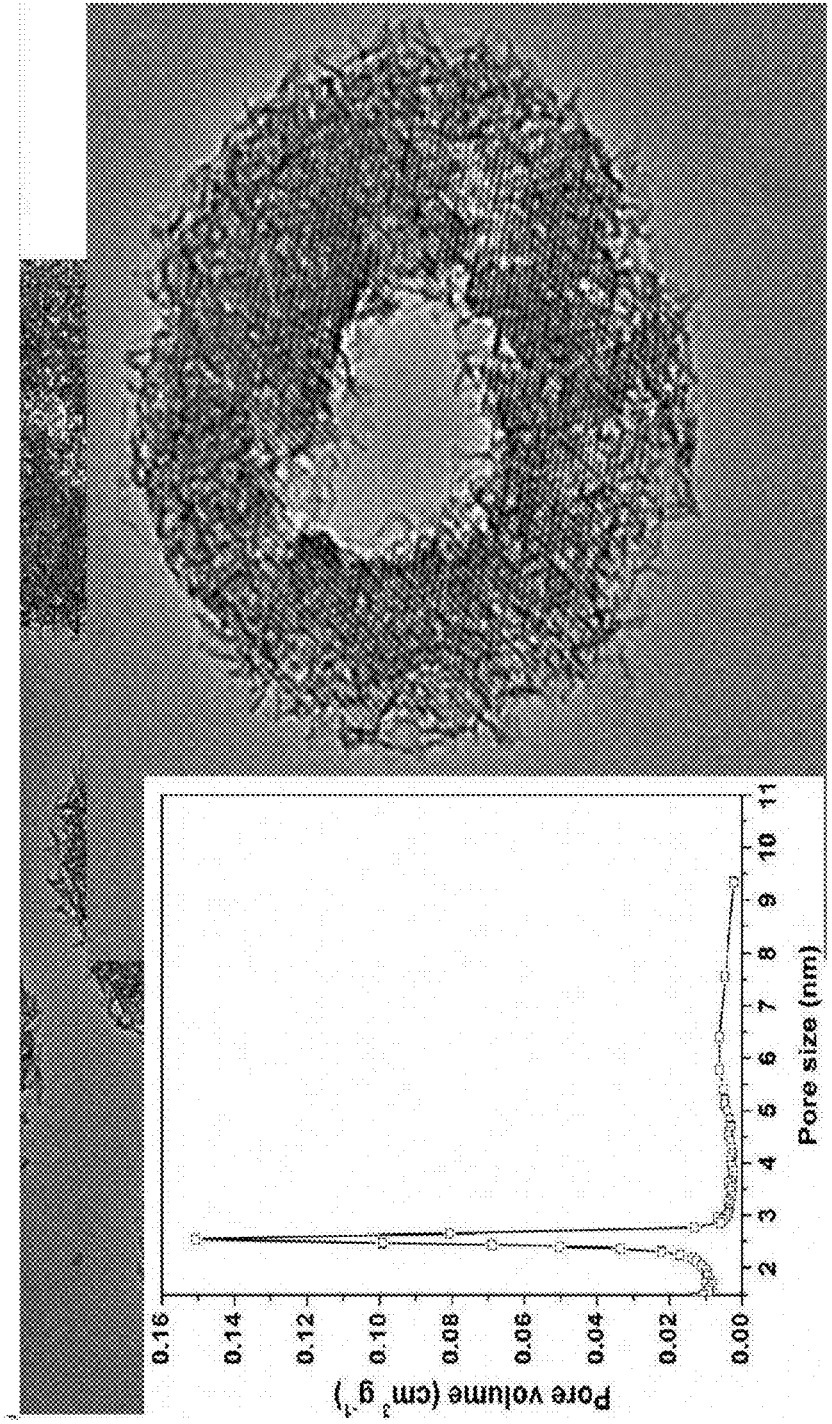
FIG. 7 shows pore size distribution and volume data for TMSNPs having large secondary pore size. As determined in the experiment(s) of Example 2.
Figure 8:
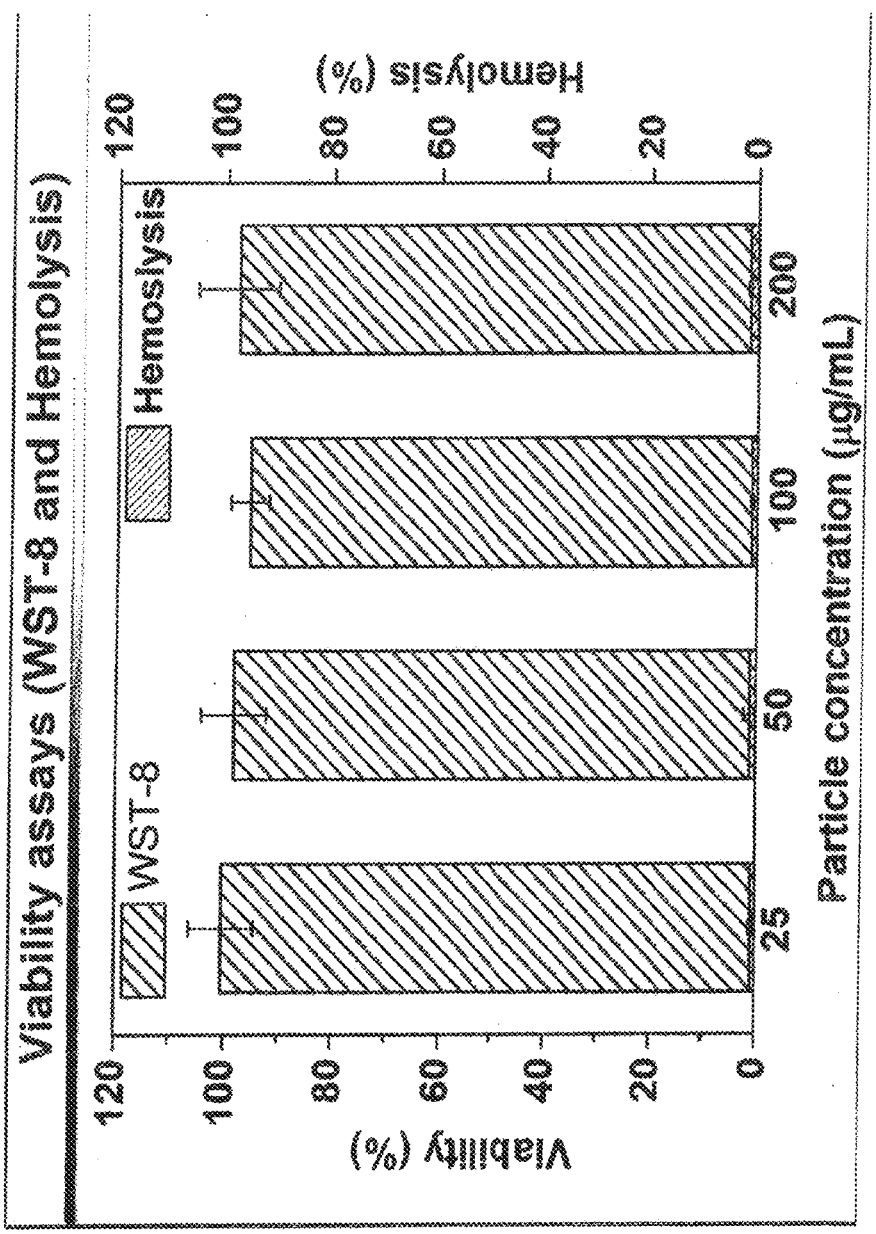
FIG. 8 depicts viability assay (WST-8 and hemolysis) data for TMSNPs made in accordance with the invention. As determined in the experiment(s) of Example 2.
Figure 9:
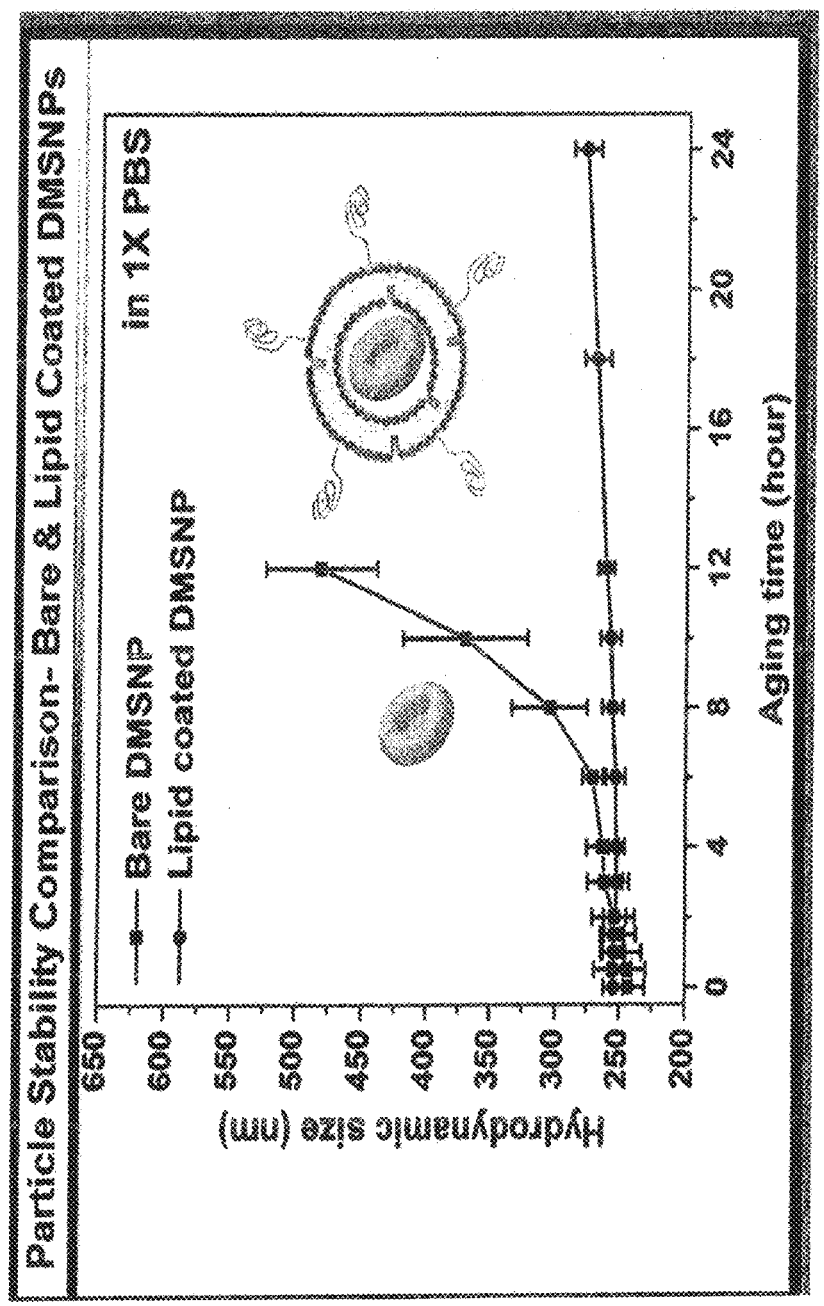
FIG. 9 compares particle stability for TMSNPs and related protocells made in accordance with the invention. As determined in the experiment(s) of Example 2.
Figure 10:
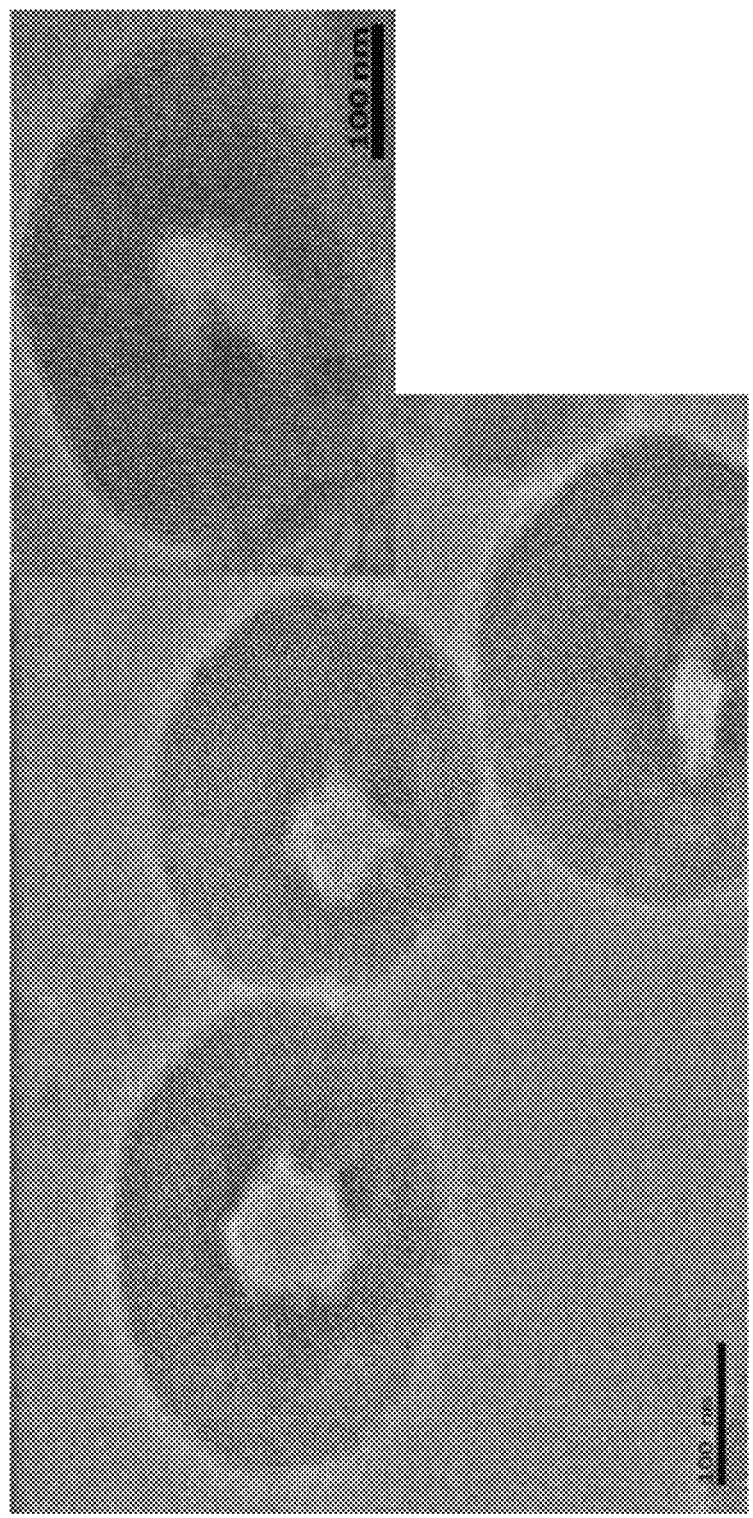
FIG. 10 is a cyro-TEM image of protocells made in accordance with the invention. As determined in the experiment(s) of Example 2.
Figure 11:
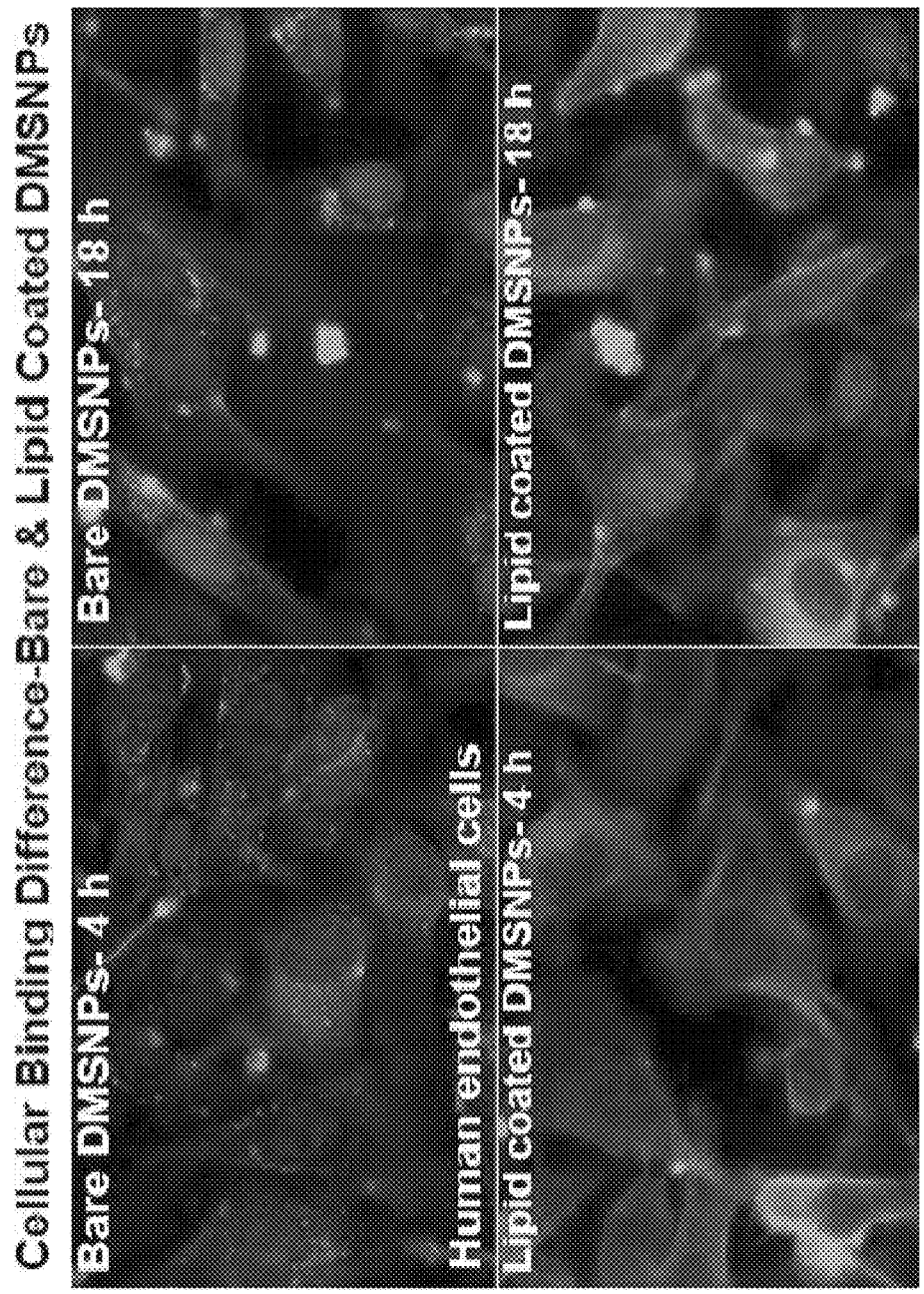
FIG. 11 depicts cellular binding differences for TMSNPs and related protocells made in accordance with the invention. As determined in the experiment(s) of Example 2.
Figure 12:
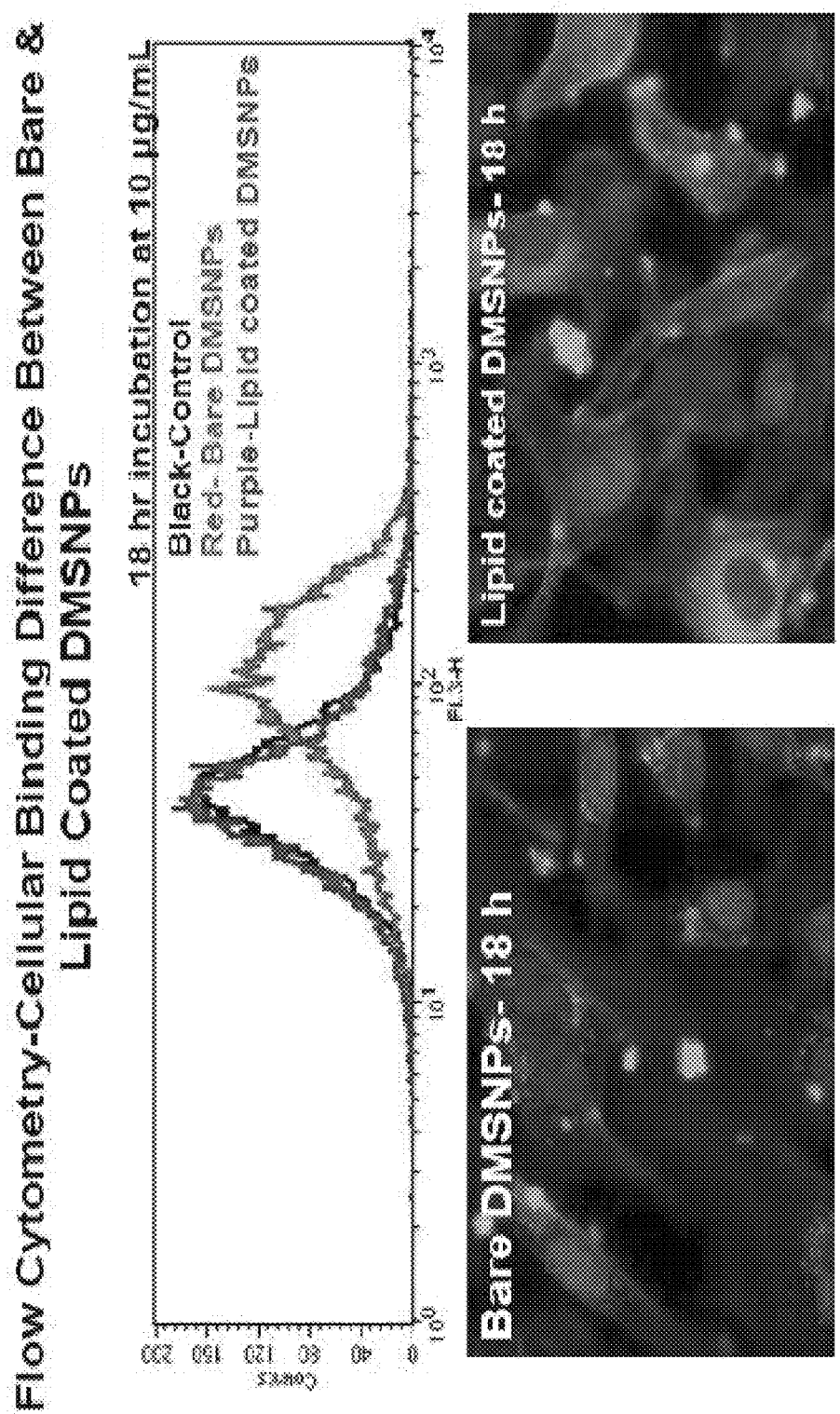
FIG. 12 depicts flow cyometry-cellular binding differences between TMSNPs and related protocells made in accordance with the invention. As determined in the experiment(s) of Example 2.
Figure 13:
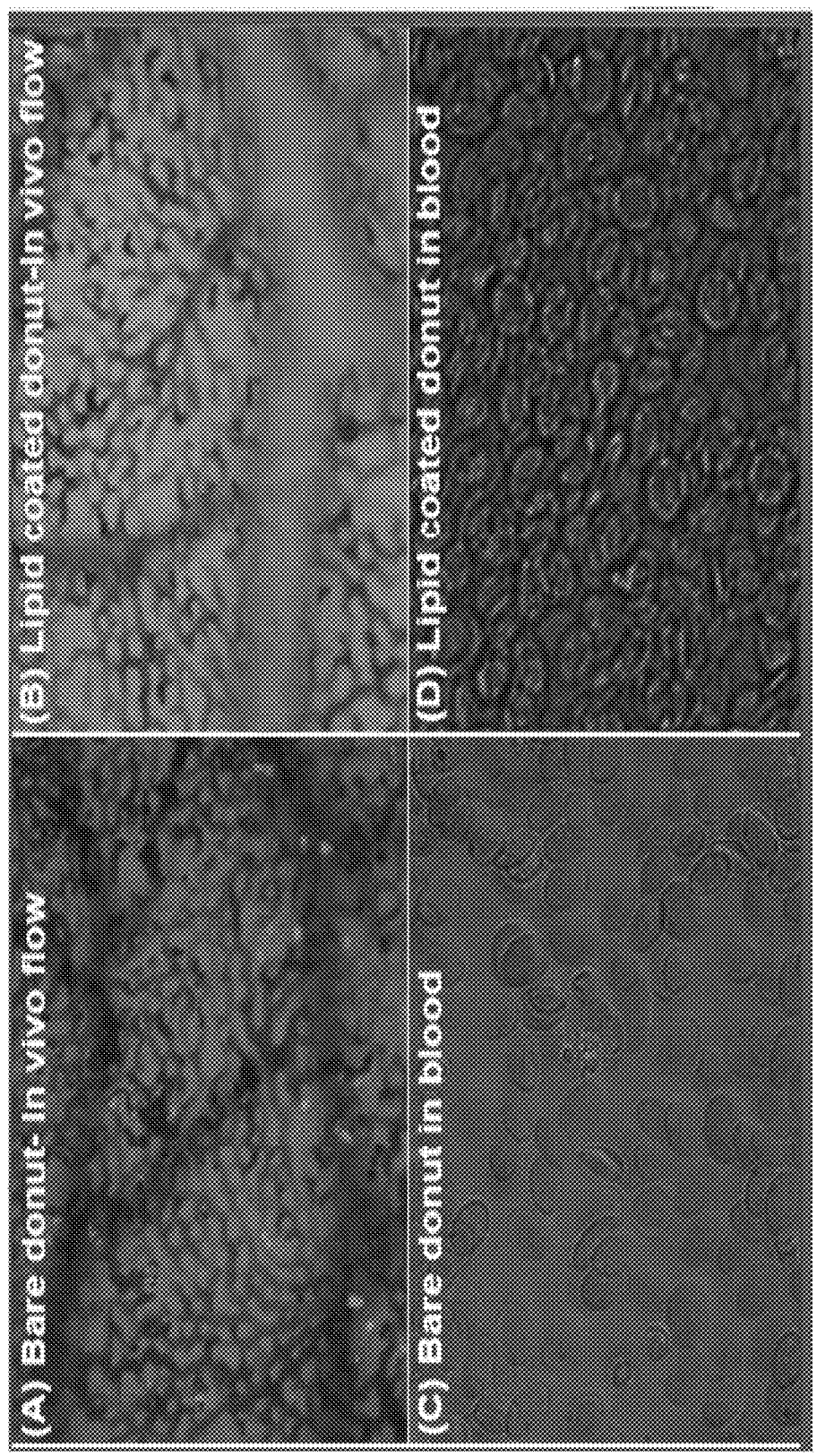
FIG. 13 depicts in vivo flow and blood cell distribution images for TMSNPs and related protocells made in accordance with the invention. As determined in the experiment(s) of Example 2.
Figure 15:
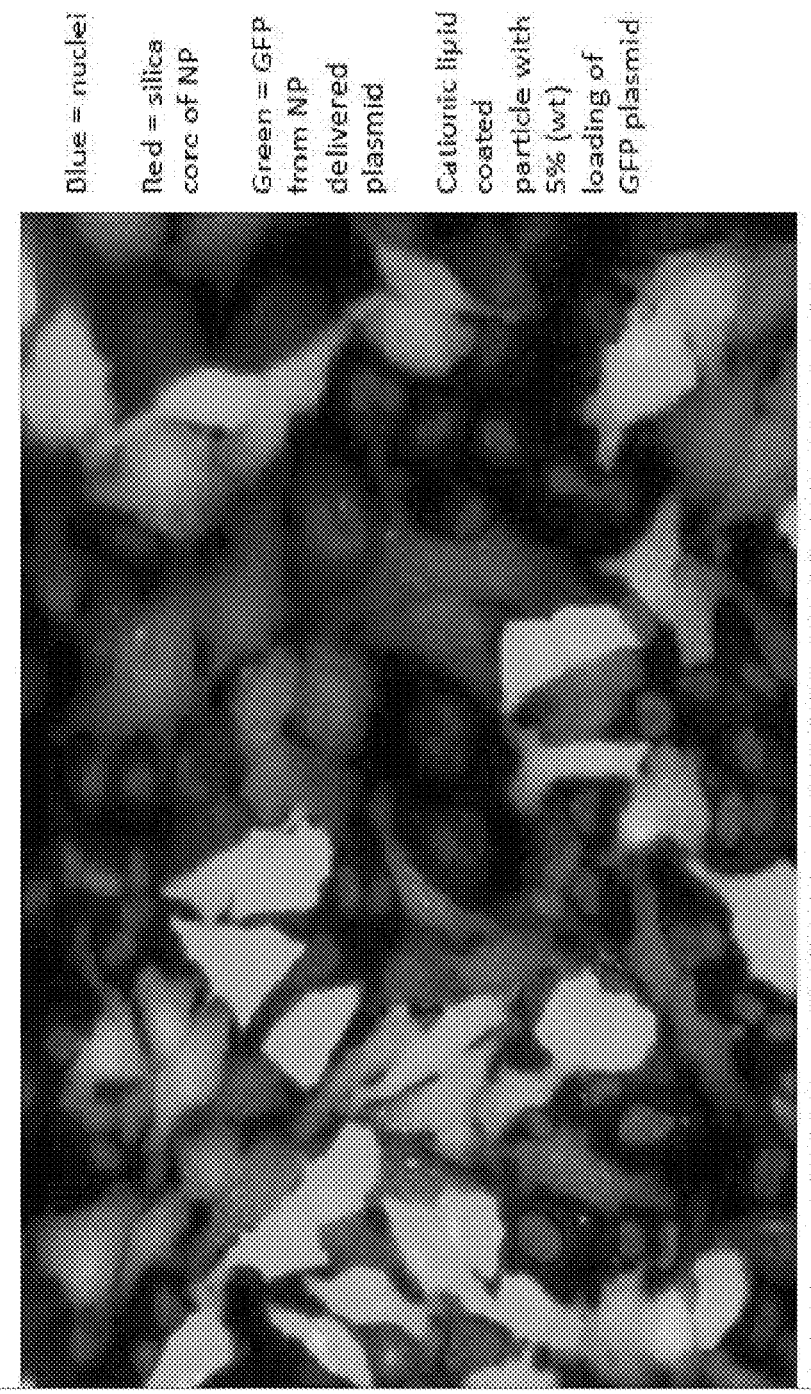
FIG. 15 illustrates HeLa cell and GFP expression of protocells made in accordance with the invention twenty-four hours following incubation at 15 ug/ml.
Figure 16:
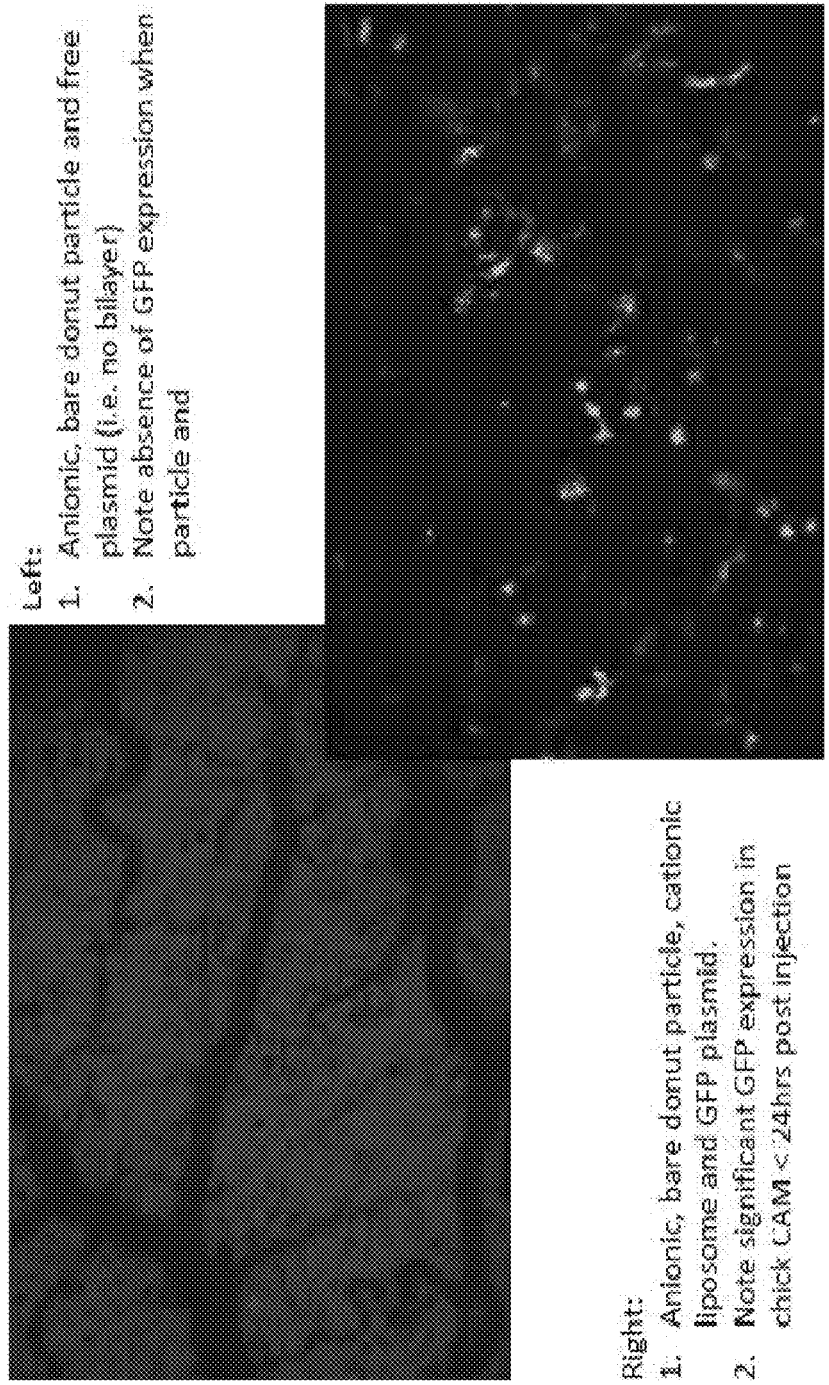
FIG. 16 depicts GFP expression in vivo of TMSNPs and related protocells made in accordance with the invention. As determined in the experiment(s) of Example 2.
Figure 17:
FIG. 17 depicts systemic GFP expression in vivo of TMSNPs and related protocells made in accordance with the invention. As determined in the experiment(s) of Example 2.
Figure 19:
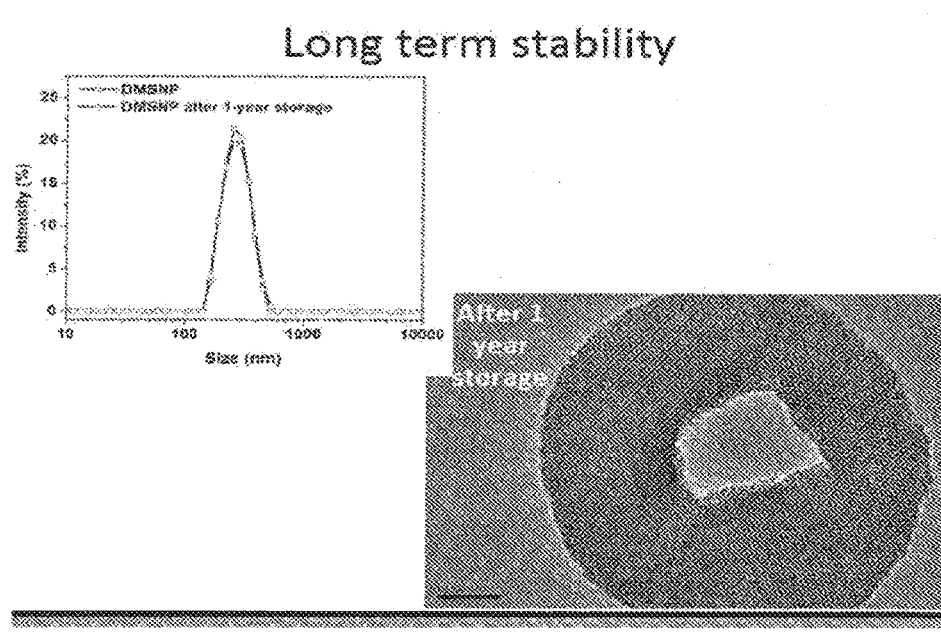
FIG. 19 reflects the long-term (one year) stability of TMSNPs made in accordance with the invention. As determined in the experiment(s) of Example 2.
Figure 20:
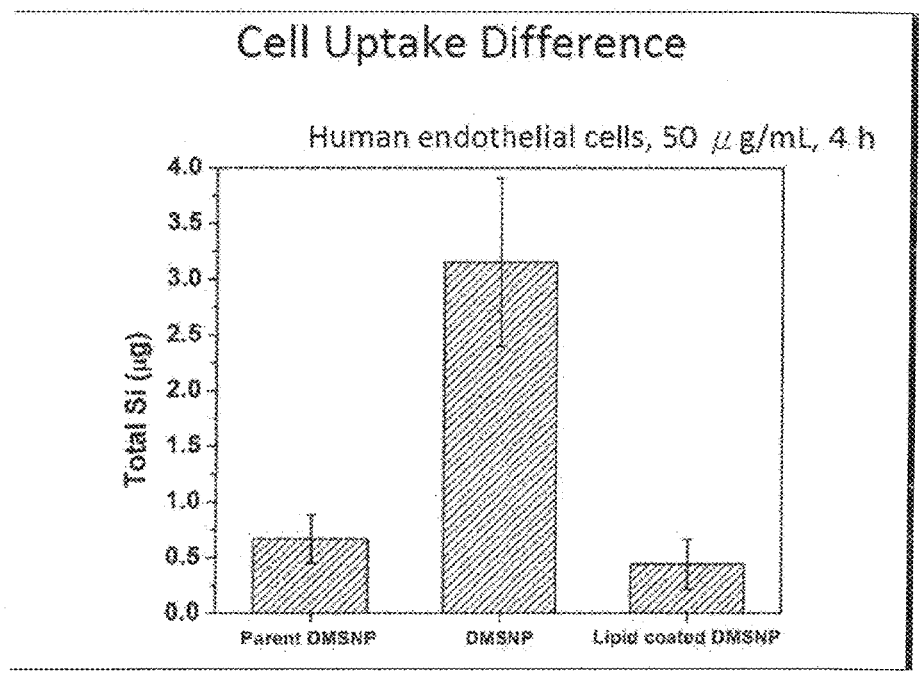
FIG. 20 compares cellular uptake differences for TMSNPs and related protocells made in accordance with the invention. As determined in the experiment(s) of Example 2.
Figure 21:
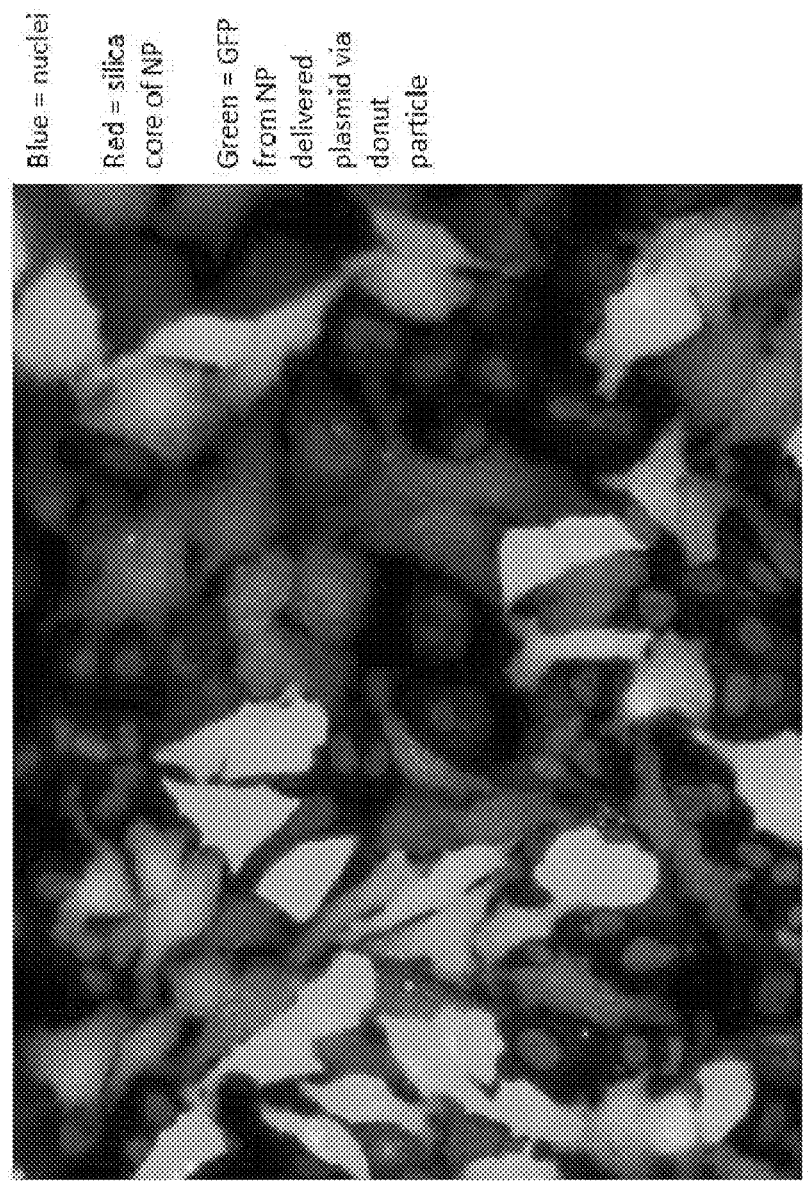
FIG. 21 depicts in vitro GFP plasmid delivery by TMSNPs made in accordance with the invention.
Figure 22:
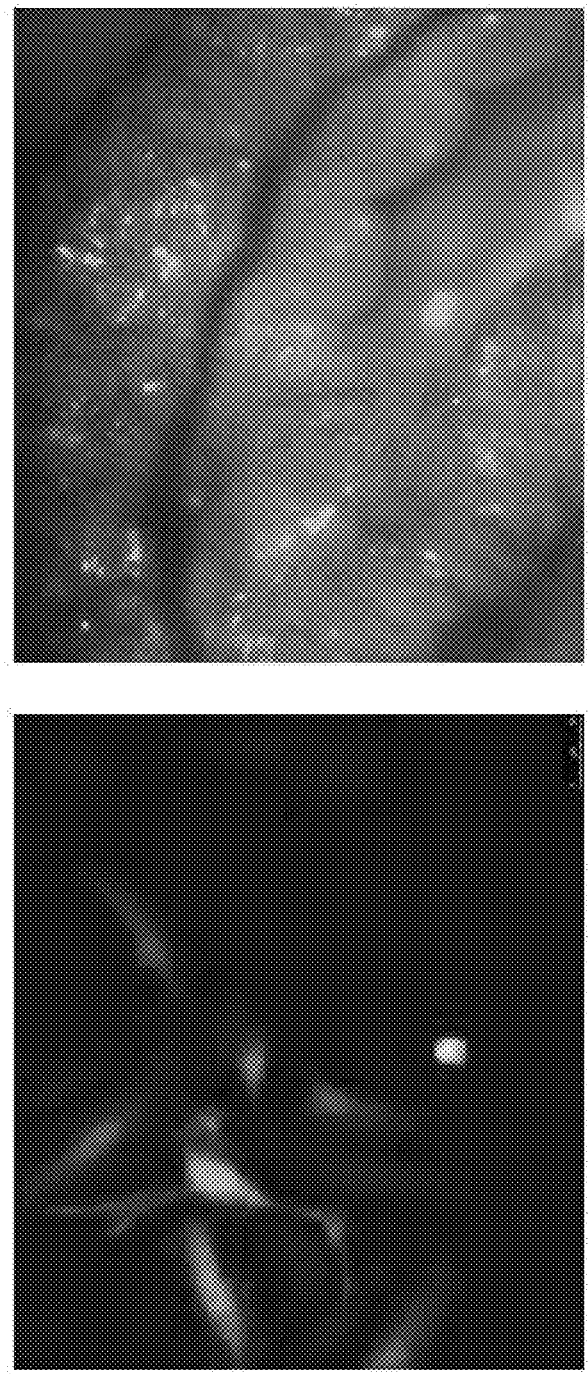
FIG. 22 illustrates systemic mRNA and in vivo nucleic acid delivery by TMSNPs and related protocells made in accordance with the invention. As determined in the experiment(s) of Example 2.
Figure 23:
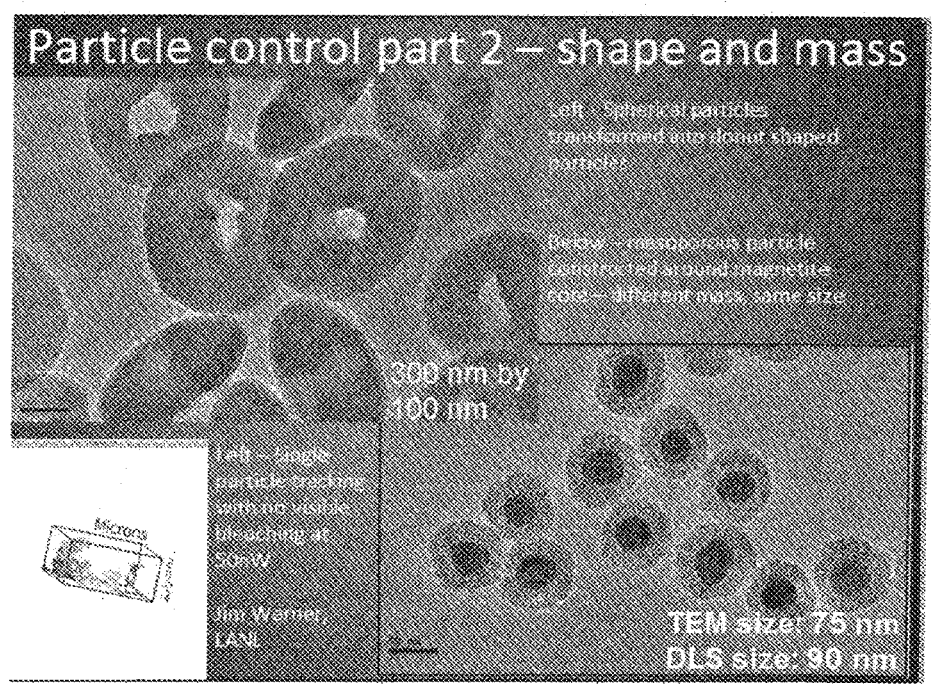
FIG. 23 shows the shape and mass of TMSNPs made in accordance with the invention.
Figure 24:
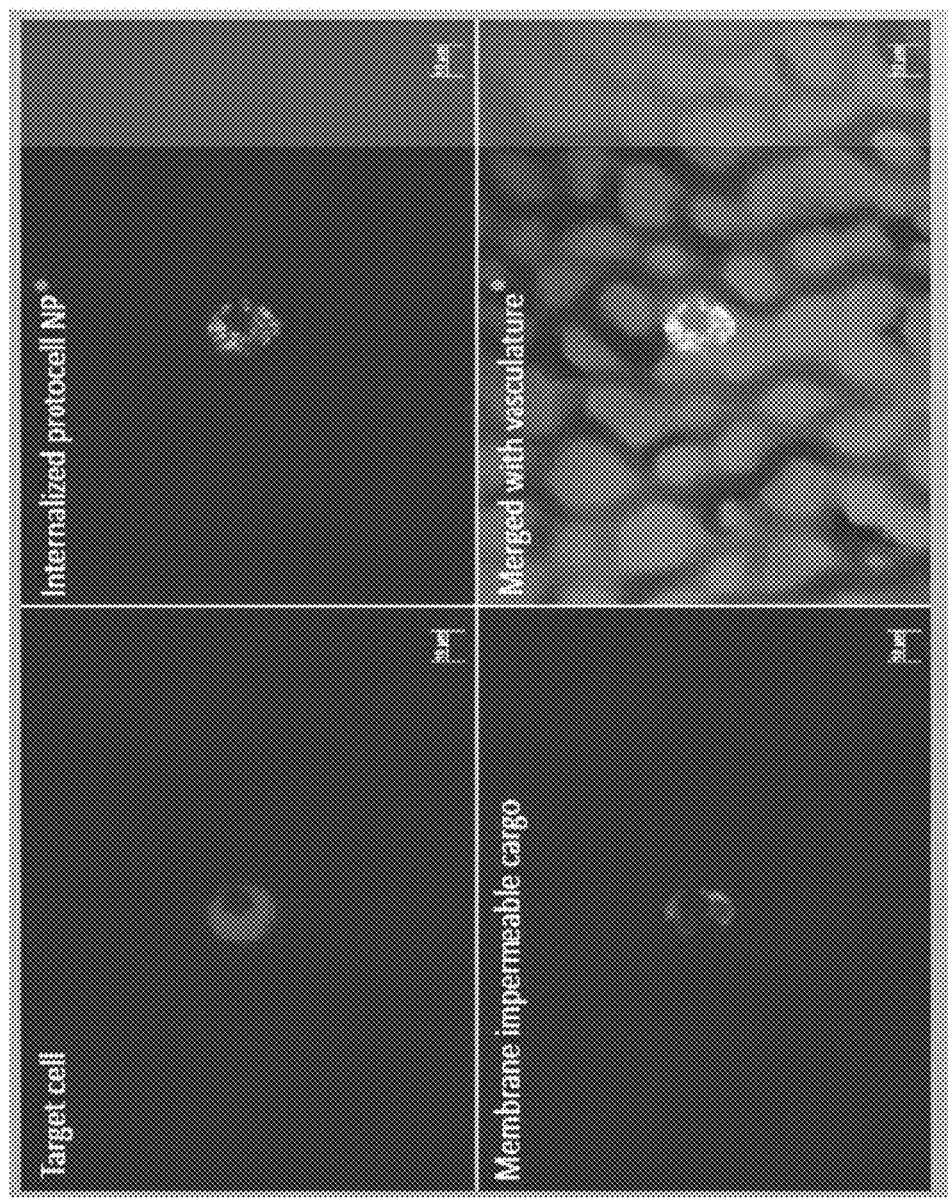
FIG. 24 shows targeted donut and cargo release in vivo. As determined in the experiment(s) of Example 2.

Mesoporous silica nanoparticles remain promising candidates for development as a nanocarrier due to the ability to control size, shape, pore structure and surface chemistry. Here we outline the synthesis of a novel torus shape mesoporous silica nanoparticle (FIGS. 18,19 and 23). This novel shape is synthesized via hydrothermal transformation of spherical particles (FIG. 18—0 hr), with an increase in size of the central pore observed over the course of 24 hrs (FIG. 18). A novel biconcave particle is also synthesized at early time points prior to formation of central pore (FIGS. 18-2 and 4 hr). Torus shaped porous silica nanoparticles exhibit a number of advantageous and unique characteristics including long shelf life (stable pore structure and shape greater than 1 year—FIG. 19), as well as enhanced cellular uptake (FIG. 20) and cargo loading (FIG. 6) relative to the precursor spherical particle. The torus particle synthesis can also be modified to yield a pore population comprised of three size ranges including the large central pore, standard 2.5 nm and larger 5-8 nm pores (FIG. 7). In addition to the unique structure of the torus particle, a change in the molecular structure can also be observed as $Si^{29}$ NMR shows an increase in $Q^4$ (and corresponding decrease in $Q^2$ and $Q^3$), indicative of a higher degree of condensation and likely responsible for the very long stability of particle and pore structure (FIG. 5). Torus particle hydrothermal transformation is not compatible with all precursor silica particles. Non-porous or isotropic pore arrangements will prevent transformation to torus (FIG. 4). However, unique MSNP structures can still be created by hydrothermal transformation of isotropic pore structure particles (FIG. 4). Low angle XRD and nitrogren adsorption/desorption isotherms were used to assess pore structure (FIG. 3). Torus particles are also observed to have no apparent toxicity in vitro (FIG. 8) or in vivo. Torus nanoparticles can be further functionalized with PEG or lipid bilayer to enhance stability in biological solutions or in vivo (FIGS. 9 and 10), or various fluorescent dyes to allow for tracking by optical imaging (FIG. 1). Bare torus particles are shown to be efficiently internalized (non-specifically) in cells in vitro (FIGS. 11 & 12) and in vivo (primarily white blood cells (F13A)—FIG. 13). However non-specific interactions can be prevented by addition of a lipid bilayer of PEG (FIG. 11-13). Cell specificity binding, internalization and cargo release have been demonstrated in vivo (FIG. 24). The unique structure of the particle also gives rise to a novel method of loading long linear molecules including mRNA and DNA, or large protein complexes, via wrapping around the particle or loading in the large central pore. This loading ability has been successfully used to transfect cells in vitro (FIG. 16,17,21) and in vivo (FIG. 22) with siRNA, mRNA, minicircle plasmid DNA and full size plasmid DNA.

References

1. Lin, Y.-S.; Tsai, C.-P.; Huang, H.-Y.; Kuo, C.-T.; Hung, Y.; Huang, D.-M.; Chen, Y.-C.; Mou, C.-Y. *Chem. Mater.* 2005, 17, 4570-4573.
2. Lin, Y.-S.; Haynes, C. L. I. *Am. Chem. Soc.* 2010, 132, 4834-4842.
3. Leong, H. S.; Steinmetz, N. F.; Ablack A.; Destito, G.; Zijlstra, A.; Stuhlmann, H.; Manchester, M; Lewis, J. D. *Nat Protoc.* 2010, 5, 1406-1417.

REFERENCES FOR BACKGROUND OF THE INVENTION (1) Nel, A. E.; Madler, L.; Velegol, D.; Xia, T.; Hoek, E. M. V.; Somasundaran, P.; Klaessig, F.; Castranova, V.; Thompson, M. *Nat. Mater* 2009, 8, 543.
(2) Albanese, A.; Tang, P. S.; Chan. W. C. W. *Annu. Rev. Biomed. Eng.* 2012, 14, 1.
(3) Dobrovolskaia, M. A.; Aggarwal, P.; Hall, J. B.; McNeil, S. E. *Mol. Pharmaceut.* 2008, 5, 487.
(4) Wang, J.; Byrne, J. D.; Napier, M. E.; DeSimone, J. M. *Small,* 2011, 14, 1919.

We claim:

1. A toroidal mesoporous silica nanoparticle (TMSNP) comprising a central cavity of about 10 nm to about 200 nm, wherein the TMSNP has a particle size of about 25 nm to about 300 nm.

2. The TMSNP of claim 1, wherein the TMSNP further comprises a plurality of pores having a pore size of about 2 nm to about 10 nm.

3. The TMSNP of claim 1, wherein the TMSNP further comprises a first plurality of pores having a pore size of about 2 nm to about 3 nm and a second plurality of pores having a pore size of about 5 nm to about 8 nm.

4. The TMSNP of claim 1, wherein the TSMNP has a surface area of between about 100 to about 1000 m²/g.

5. The TMSNP of claim 1, wherein the TMSNP has a Zeta potential of between about −40 mV to about +40 mV.

6. The TMSNP of claim 1, wherein the TMSNP is further coated with a lipid bilayer.

7. The TMSNP of claim 1 wherein the TMSNP is further modified with SiOH or polyethylene glycol (PEG).

8. The TMSNP of claim 1 wherein the TMSNP is aminated.

9. The TMSNP of claim 1 wherein the TMSNP is loaded with cargo.

10. The TMSNP of claim 9 wherein the cargo is a nucleic acid of at least about 1000 nucleotides in length, is nucleic acid that is naked, is minicircle DNA, is mRNA or is cDNA.

11. The TMSNP of claim 9, wherein the cargo is a protein having molecular weight of at least about 40 kDa, is a multimeric protein, is a protein complex, is an antibody or a fragment thereof, is an enzyme or is a transmembrane receptor.

12. The TMSNP of claim 1, further comprising a targeting ligand.

13. A method of treating a disease in an individual by administering to the individual an effective amount of a pharmaceutical composition comprising the TMSNP of claim 1, wherein the TMSNP in the pharmaceutical composition is loaded with a cargo.

14. A method of making a toroidal mesoporous silica nanoparticle (TMSNP) comprising a central cavity of about 10 nm to about 200 nm, wherein the TMSNP has a particle size of about 25 nm to about 300 nm, the method comprising hydrothermally treating a ellipsoid shaped mesoporous silica particle by heating the particle at a temperature of between about 100° C. to about 150° C.

15. The method of claim 14, wherein the method further comprises loading the particle formed as a result of the hydrothermal treatment with a cargo.

16. The method of claim 14, wherein the method further comprises coating the particle formed as a result of the hydrothermal treatment with a lipid bilayer.

17. The method of claim 14, wherein the ellipsoid shaped mesoporous silica particle is produced by using a ammonia base-catalyzed method under a low surfactant concentration.

18. The method of claim 17, wherein the ammonia base-catalyzed method comprises the step of reacting tetraethyl orthosilicate (TEOS) with a mixture of n-cetyltrimethlammonium bromide (CTAB) and NH4OH.

* * * * *

SEQUENCE LISTING

<160> NUMBER OF SEQ ID NOS: 4

<210> SEQ ID NO 1
<211> LENGTH: 42
<212> TYPE: PRT
<213> ORGANISM: Artificial Sequence
<220> FEATURE:
<223> OTHER INFORMATION: A synthetic amino acid sequence

<400> SEQUENCE: 1

-continued

```
Gly Asn Gln Ser Ser Asn Phe Gly Pro Met Lys Gly Gly Asn Phe Gly
 1               5                  10                  15

Gly Arg Ser Ser Gly Pro Tyr Gly Gly Gly Gln Tyr Phe Ala Lys
                20                  25              30

Pro Arg Asn Gln Gly Gly Tyr Gly Gly Cys
                35                  40

<210> SEQ ID NO 2
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 2

Arg Arg Met Lys Trp Lys Lys
 1               5

<210> SEQ ID NO 3
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 3

Pro Lys Lys Lys Arg Lys Val
 1               5

<210> SEQ ID NO 4
<211> LENGTH: 16
<212> TYPE: PRT
<213> ORGANISM: Artificial Sequence
<220> FEATURE:
<223> OTHER INFORMATION: A synthetic amino acid sequence

<400> SEQUENCE: 4

Lys Arg Pro Ala Ala Thr Lys Lys Ala Gly Gln Ala Lys Lys Lys Lys
 1               5                  10                  15
```

UNITED STATES PATENT AND TRADEMARK OFFICE
CERTIFICATE OF CORRECTION

PATENT NO. : 9,855,217 B2
APPLICATION NO. : 15/023110
DATED : January 2, 2018
INVENTOR(S) : Brinker et al.

Page 1 of 1

It is certified that error appears in the above-identified patent and that said Letters Patent is hereby corrected as shown below:

In the Claims

In Column 30, Line 64, in Claim 14, delete "100° C. to about 150° C." and insert --100 °C. to about 150 °C.-- therefor In Column 31, Lines 9-10, in Claim 18, delete "n-cetyltrimethlammonium" and insert --n-cetyltrimethylammonium-- therefor In Column 31, Line 10, in Claim 18, delete "NH4OH." and insert --NH$_4$OH.-- therefor Signed and Sealed this
Twenty-fifth Day of June, 2019

Andrei Iancu
*Director of the United States Patent and Trademark Office*